(12) United States Patent
Xia et al.

(10) Patent No.: US 9,147,037 B2
(45) Date of Patent: Sep. 29, 2015

(54) AUTOMATED ANALYSIS OF MULTIPLEXED PROBE-TARGET INTERACTION PATTERNS: PATTERN MATCHING AND ALLELE IDENTIFICATION

(75) Inventors: Xiongwu Xia, Dayton, NJ (US); Michael Seul, Fanwood, NJ (US)

(73) Assignee: BioArray Solutions, Ltd., Warren, NJ (US)

( * ) Notice: Subject to any disclaimer, the term of this patent is extended or adjusted under 35 U.S.C. 154(b) by 0 days.

(21) Appl. No.: 13/297,487

(22) Filed: Nov. 16, 2011

(65) Prior Publication Data

US 2012/0065099 A1 Mar. 15, 2012

Related U.S. Application Data

(63) Continuation of application No. 12/961,086, filed on Dec. 6, 2010, now abandoned, which is a continuation of application No. 10/909,638, filed on Aug. 2, 2004, now Pat. No. 7,848,889.

(51) Int. Cl.
*G06F 19/20* (2011.01)
*C12Q 1/68* (2006.01)
*G06F 19/18* (2011.01)

(52) U.S. Cl.
CPC ..................................... *G06F 19/18* (2013.01)

(58) Field of Classification Search
CPC .... C12Q 1/686; C12Q 1/6841; C12Q 1/6858; C12Q 1/6827; C12Q 2600/156; C12Q 1/6813; G01N 2333/70539; G06F 19/18; G06F 19/20
See application file for complete search history.

(56) References Cited

U.S. PATENT DOCUMENTS

| | | |
|---|---|---|
| 3,329,638 A | 7/1967 | Blyth |
| 3,574,614 A | 4/1971 | Carreira |
| 3,790,492 A | 2/1974 | Fulwyler |
| 3,957,741 A | 5/1976 | Rembaum et al. |
| 3,982,182 A | 9/1976 | Hogg |
| 3,989,775 A | 11/1976 | Jack et al. |
| 3,998,525 A | 12/1976 | Giglia |
| 4,003,713 A | 1/1977 | Bowser |
| 4,046,667 A | 9/1977 | Goetz |
| 4,055,799 A | 10/1977 | Coster et al. |
| 4,075,013 A | 2/1978 | Ward et al. |
| 4,102,990 A | 7/1978 | Uzgiris |
| 4,140,937 A | 2/1979 | Vecht et al. |
| 4,143,203 A | 3/1979 | Rigopulos et al. |
| 4,199,363 A | 4/1980 | Chen |
| 4,258,001 A | 3/1981 | Pierce et al. |
| 4,267,235 A | 5/1981 | Rembaum et al. |
| 4,275,053 A | 6/1981 | Rosenfield et al. |
| 4,326,008 A | 4/1982 | Rembaum |
| 4,336,173 A | 6/1982 | Ugelstad |
| 4,339,337 A | 7/1982 | Tricot et al. |
| 4,358,388 A | 11/1982 | Daniel et al. |
| 4,383,529 A | 5/1983 | Webster |
| 4,421,896 A | 12/1983 | Dorman |
| 4,456,513 A | 6/1984 | Kawai et al. |
| 4,459,378 A | 7/1984 | Ugelstad |
| 4,487,855 A | 12/1984 | Shih et al. |
| 4,497,208 A | 2/1985 | Oja et al. |
| 4,499,052 A | 2/1985 | Fulwyler |
| 4,575,407 A | 3/1986 | Diller |
| 4,591,550 A | 5/1986 | Hafeman et al. |
| 4,602,989 A | 7/1986 | Culkin |
| 4,613,559 A | 9/1986 | Ober et al. |
| 4,647,544 A | 3/1987 | Nicoli et al. |
| 4,654,267 A | 3/1987 | Ugelstad et al. |
| 4,663,408 A | 5/1987 | Schulz et al. |
| 4,665,020 A | 5/1987 | Saunders |
| 4,672,040 A | 6/1987 | Josephson |
| 4,679,439 A | 7/1987 | Culkin |
| 4,680,332 A | 7/1987 | Hair et al. |
| 4,702,598 A | 10/1987 | Böhmer |
| 4,717,655 A | 1/1988 | Fulwyler |
| 4,753,775 A | 6/1988 | Ebersole et al. |
| 4,774,189 A | 9/1988 | Schwartz |
| 4,774,265 A | 9/1988 | Ugelstad et al. |
| 4,791,310 A | 12/1988 | Honig et al. |

(Continued)

FOREIGN PATENT DOCUMENTS

| | | |
|---|---|---|
| CA | 1248873 | 1/1989 |
| DE | 4035714 | 5/1992 |

(Continued)

OTHER PUBLICATIONS

Saiki et al. Genetic analysis of amplified DNA with immobilized sequence-specific oligonucleotide probes Proceedings of the National Academy of Sciences USA vol. 86, pp. 6230-6234 (1989).*
Duquesnoy "HLAMatchmaker: A Molecularly Based Algorithm for Histocompatibility Determination. I. Description of the Algorithm" *Human Immunology* (2002) vol. 63 p. 339-352.
Gerlach "Human Lymphocyte Antigen Molecular Typing" Archives of Pathology & Laboratory Medicine (Mar. 2002) vol. 126 p. 281-284.
Guo et al. "Oligonucleotide Arrays for High-Throughput SNPs Detection in the MHC Class I Genes: HLA-B as a Model System" *Genome Research*, Cold Spring Harbor laboratory Press, Woodbury, NY (Mar. 2002) vol. 12 No. 3 p. 447-457.
Mei et al. "Genome-wide Detection of Allelic Imbalance Using human SNPs and high-density DNA Arrays" Genome Research Cold Spring Harbor laboratory Press (2000) vol. 10 p. 1126-1137.
Pastinen et al. "A System for Specific, High-throughput Genotyping by Allele-Specific Primer Extension on Microarrays" *Genome Research*, Cold Spring Harbor laboratory Press (2000) vol. 10 p. 1031-1042.

(Continued)

*Primary Examiner* — John S Brusca
(74) *Attorney, Agent, or Firm* — Mintz, Levin, Cohn, Ferris, Glovsky and Popeo, P.C.

(57) ABSTRACT

Methods and algorithms for automated allele assignments within an integrated software environment are provided. These methods and algorithms offer a multiplicity of functionalities including: data management; system configuration including user authorization, training set analysis and probe masking; pattern analysis including string matching and probe flipping; and interactive redaction of data. The methods and algorithms further include methods of setting thresholds, refining thresholds, and probe masking of signals produced by probes which do not contribute significantly to discriminating among alleles.

2 Claims, 12 Drawing Sheets

(56) References Cited

U.S. PATENT DOCUMENTS

| | | |
|---|---|---|
| 4,795,698 A | 1/1989 | Owen et al. |
| 4,806,313 A | 2/1989 | Ebersole et al. |
| 4,806,776 A | 2/1989 | Kley |
| 4,822,746 A | 4/1989 | Walt |
| 4,824,941 A | 4/1989 | Gordon et al. |
| 4,829,101 A | 5/1989 | Kraemer et al. |
| 4,832,814 A | 5/1989 | Root |
| 4,851,331 A | 7/1989 | Vary et al. |
| 4,873,102 A | 10/1989 | Chang et al. |
| 4,891,324 A | 1/1990 | Pease et al. |
| 4,911,806 A | 3/1990 | Hofmann |
| 4,920,056 A | 4/1990 | Dasgupta |
| 4,994,373 A | 2/1991 | Stavrianopoulos et al. |
| 4,996,265 A | 2/1991 | Okubo et al. |
| 5,002,867 A | 3/1991 | Macevicz |
| 5,015,452 A | 5/1991 | Matijevic |
| 5,028,545 A | 7/1991 | Soini |
| 5,073,498 A | 12/1991 | Schwartz et al. |
| 5,075,217 A | 12/1991 | Weber |
| 5,091,206 A | 2/1992 | Wang et al. |
| 5,105,305 A | 4/1992 | Betzig et al. |
| 5,114,864 A | 5/1992 | Walt |
| 5,126,239 A | 6/1992 | Livak et al. |
| 5,128,006 A | 7/1992 | Mitchell et al. |
| 5,132,097 A | 7/1992 | Van Deusen et al. |
| 5,132,242 A | 7/1992 | Cheung |
| 5,143,853 A | 9/1992 | Walt |
| 5,143,854 A | 9/1992 | Pirrung et al. |
| 5,147,777 A | 9/1992 | Sutton et al. |
| 5,155,044 A | 10/1992 | Ledis et al. |
| 5,173,159 A | 12/1992 | Dutertre |
| 5,185,066 A | 2/1993 | Golias |
| 5,187,096 A | 2/1993 | Giaever et al. |
| 5,194,300 A | 3/1993 | Cheung |
| 5,194,393 A | 3/1993 | Hugl et al. |
| 5,208,111 A | 5/1993 | Decher et al. |
| 5,221,417 A | 6/1993 | Basavanhally |
| 5,234,809 A | 8/1993 | Boom et al. |
| 5,241,012 A | 8/1993 | Clark |
| 5,244,630 A | 9/1993 | Khalil et al. |
| 5,244,636 A | 9/1993 | Walt et al. |
| 5,244,813 A | 9/1993 | Walt et al. |
| 5,250,264 A | 10/1993 | Walt et al. |
| 5,252,494 A | 10/1993 | Walt |
| 5,254,477 A | 10/1993 | Walt |
| 5,266,238 A | 11/1993 | Haacke et al. |
| 5,266,427 A | 11/1993 | Iwase et al. |
| 5,266,497 A | 11/1993 | Imai et al. |
| 5,281,370 A | 1/1994 | Asher et al. |
| 5,283,079 A | 2/1994 | Wang et al. |
| 5,288,577 A | 2/1994 | Yamaguchi et al. |
| 5,298,741 A | 3/1994 | Walt et al. |
| 5,301,044 A | 4/1994 | Wright |
| 5,306,618 A | 4/1994 | Prober et al. |
| 5,308,586 A | 5/1994 | Fritsche et al. |
| 5,308,749 A | 5/1994 | Sutton et al. |
| 5,320,814 A | 6/1994 | Walt et al. |
| 5,326,691 A | 7/1994 | Hozier |
| 5,326,692 A | 7/1994 | Brinkley et al. |
| 5,329,461 A | 7/1994 | Allen et al. |
| 5,348,853 A | 9/1994 | Wang et al. |
| 5,356,713 A | 10/1994 | Charmot et al. |
| 5,362,653 A | 11/1994 | Carr et al. |
| 5,364,759 A | 11/1994 | Caskey et al. |
| 5,382,512 A | 1/1995 | Smethers et al. |
| 5,382,801 A | 1/1995 | Kanayama |
| 5,389,549 A | 2/1995 | Hamaguchi et al. |
| 5,395,688 A | 3/1995 | Wang et al. |
| 5,405,784 A | 4/1995 | Van Hoegaerden |
| 5,412,087 A | 5/1995 | McGall et al. |
| 5,415,835 A | 5/1995 | Brueck et al. |
| 5,422,246 A | 6/1995 | Koopal et al. |
| 5,436,327 A | 7/1995 | Southern et al. |
| 5,442,246 A | 8/1995 | Azegami et al. |
| 5,444,330 A | 8/1995 | Leventis et al. |
| 5,447,440 A | 9/1995 | Davis et al. |
| 5,468,649 A | 11/1995 | Shah et al. |
| 5,470,534 A | 11/1995 | Imai et al. |
| 5,474,796 A | 12/1995 | Brennan |
| 5,474,895 A | 12/1995 | Ishii et al. |
| 5,480,723 A | 1/1996 | Klainer et al. |
| 5,488,567 A | 1/1996 | Allen et al. |
| 5,496,997 A | 3/1996 | Pope |
| 5,498,392 A | 3/1996 | Wilding et al. |
| 5,510,270 A | 4/1996 | Fodor et al. |
| 5,512,157 A | 4/1996 | Guadagno et al. |
| 5,512,439 A | 4/1996 | Hornes et al. |
| 5,512,490 A | 4/1996 | Walt et al. |
| 5,514,785 A | 5/1996 | VanNess et al. |
| 5,516,635 A | 5/1996 | Ekins et al. |
| 5,518,883 A | 5/1996 | Soini |
| 5,523,231 A | 6/1996 | Reeve |
| 5,527,710 A | 6/1996 | Nacamulli et al. |
| 5,528,392 A | 6/1996 | Nakagawa et al. |
| 5,532,128 A | 7/1996 | Eggers et al. |
| 5,536,648 A | 7/1996 | Kemp et al. |
| 5,545,522 A | 8/1996 | Van Gelder et al. |
| 5,545,531 A | 8/1996 | Rava et al. |
| 5,552,086 A | 9/1996 | Siiman et al. |
| 5,552,270 A | 9/1996 | Khrapko et al. |
| 5,556,752 A | 9/1996 | Lockhart et al. |
| 5,565,324 A | 10/1996 | Still et al. |
| 5,567,304 A | 10/1996 | Datta et al. |
| 5,567,627 A | 10/1996 | Lehnen |
| 5,573,909 A | 11/1996 | Singer et al. |
| 5,582,988 A | 12/1996 | Backus et al. |
| 5,585,069 A | 12/1996 | Zanzucchi et al. |
| 5,587,128 A | 12/1996 | Wilding et al. |
| 5,593,838 A | 1/1997 | Zanzucchi et al. |
| 5,593,839 A | 1/1997 | Hubbell et al. |
| 5,602,042 A | 2/1997 | Farber |
| 5,604,097 A | 2/1997 | Brenner |
| 5,604,099 A | 2/1997 | Erlich et al. |
| 5,610,287 A | 3/1997 | Nikiforov et al. |
| 5,627,040 A | 5/1997 | Bierre et al. |
| 5,632,957 A | 5/1997 | Heller et al. |
| 5,633,724 A | 5/1997 | King et al. |
| 5,633,972 A | 5/1997 | Walt et al. |
| 5,637,508 A | 6/1997 | Kidwell et al. |
| 5,639,603 A | 6/1997 | Dower et al. |
| 5,639,606 A | 6/1997 | Wiley |
| 5,643,765 A | 7/1997 | Wiley |
| 5,648,124 A | 7/1997 | Sutor |
| 5,650,488 A | 7/1997 | O'Hare |
| 5,650,489 A | 7/1997 | Lam et al. |
| 5,652,059 A | 7/1997 | Margel |
| 5,652,107 A | 7/1997 | Lizardi et al. |
| 5,653,939 A | 8/1997 | Hollis et al. |
| 5,660,990 A | 8/1997 | Rao et al. |
| 5,667,667 A | 9/1997 | Southern |
| 5,674,686 A | 10/1997 | Schumm et al. |
| 5,674,698 A | 10/1997 | Zarling et al. |
| 5,679,524 A | 10/1997 | Nikiforov et al. |
| 5,690,894 A | 11/1997 | Pinkel et al. |
| 5,698,271 A | 12/1997 | Liberti et al. |
| 5,700,637 A | 12/1997 | Southern |
| 5,700,897 A | 12/1997 | Klainer et al. |
| 5,714,340 A | 2/1998 | Sutton et al. |
| 5,714,521 A | 2/1998 | Kedem et al. |
| 5,716,852 A | 2/1998 | Yager et al. |
| 5,722,470 A | 3/1998 | Kedar et al. |
| 5,723,218 A | 3/1998 | Haugland et al. |
| 5,723,233 A | 3/1998 | Garza et al. |
| 5,728,529 A | 3/1998 | Metzker et al. |
| 5,736,349 A | 4/1998 | Sasaki et al. |
| 5,744,299 A | 4/1998 | Henrickson et al. |
| 5,744,305 A | 4/1998 | Fodor et al. |
| 5,747,349 A | 5/1998 | Van den Engh et al. |
| 5,751,629 A | 5/1998 | Nova et al. |
| 5,763,175 A | 6/1998 | Brenner |
| 5,763,198 A | 6/1998 | Hirth et al. |
| 5,763,263 A | 6/1998 | Dehlinger |
| 5,766,711 A | 6/1998 | Barmakian |
| 5,766,963 A | 6/1998 | Baldwin et al. |

(56) References Cited

U.S. PATENT DOCUMENTS

| | | | |
|---|---|---|---|
| 5,770,358 | A | 6/1998 | Dower et al. |
| 5,770,367 | A | 6/1998 | Southern et al. |
| 5,770,455 | A | 6/1998 | Cargill et al. |
| 5,770,721 | A | 6/1998 | Ershov et al. |
| 5,773,222 | A | 6/1998 | Scott |
| 5,776,711 | A | 7/1998 | Vyas et al. |
| 5,779,976 | A | 7/1998 | Leland et al. |
| 5,786,219 | A | 7/1998 | Zhang et al. |
| 5,789,147 | A | 8/1998 | Rubinstein et al. |
| 5,792,430 | A | 8/1998 | Hamper |
| 5,800,992 | A | 9/1998 | Fodor et al. |
| 5,807,755 | A | 9/1998 | Ekins |
| 5,812,272 | A | 9/1998 | King et al. |
| 5,814,524 | A | 9/1998 | Walt et al. |
| 5,831,045 | A | 11/1998 | Stolowitz et al. |
| 5,834,590 | A | 11/1998 | Vinik et al. |
| 5,837,501 | A | 11/1998 | Beumer et al. |
| 5,837,551 | A | 11/1998 | Ekins |
| 5,837,832 | A | 11/1998 | Chee et al. |
| 5,840,485 | A | 11/1998 | Lebl et al. |
| 5,843,660 | A | 12/1998 | Schumm et al. |
| 5,844,304 | A | 12/1998 | Kata et al. |
| 5,846,708 | A | 12/1998 | Hollis et al. |
| 5,855,753 | A | 1/1999 | Trau et al. |
| 5,856,092 | A | 1/1999 | Dale et al. |
| 5,858,804 | A | 1/1999 | Zanzucchi et al. |
| 5,866,099 | A | 2/1999 | Owen et al. |
| 5,866,331 | A | 2/1999 | Singer et al. |
| 5,874,219 | A | 2/1999 | Rava et al. |
| 5,876,946 | A | 3/1999 | Burbaum et al. |
| 5,898,071 | A | 4/1999 | Hawkins |
| 5,900,481 | A | 5/1999 | Lough et al. |
| 5,922,617 | A | 7/1999 | Wang et al. |
| 5,939,021 | A | 8/1999 | Hansen et al. |
| 5,942,388 | A | 8/1999 | Willner et al. |
| 5,945,525 | A | 8/1999 | Uematsu et al. |
| 5,948,621 | A | 9/1999 | Turner et al. |
| 5,948,627 | A | 9/1999 | Lee et al. |
| 5,952,131 | A | 9/1999 | Kumacheva et al. |
| 5,952,174 | A | 9/1999 | Nikiforoy et al. |
| 5,959,098 | A | 9/1999 | Goldberg et al. |
| 5,961,923 | A | 10/1999 | Nova et al. |
| 5,965,235 | A | 10/1999 | McGuire et al. |
| 5,965,452 | A | 10/1999 | Kovacs |
| 5,968,736 | A | 10/1999 | Still et al. |
| 5,981,176 | A | 11/1999 | Wallace |
| 5,981,180 | A | 11/1999 | Chandler et al. |
| 5,988,432 | A | 11/1999 | Sun |
| 5,989,835 | A | 11/1999 | Dunlay et al. |
| 5,993,935 | A | 11/1999 | Rasmussen et al. |
| 5,994,066 | A | 11/1999 | Bergeron et al. |
| 6,001,614 | A | 12/1999 | Akhavan-Tafti |
| 6,004,744 | A | 12/1999 | Goelet et al. |
| 6,007,996 | A | 12/1999 | McNamara et al. |
| 6,013,531 | A | 1/2000 | Wang et al. |
| 6,014,451 | A | 1/2000 | Berry et al. |
| 6,015,664 | A | 1/2000 | Henrickson et al. |
| 6,015,666 | A | 1/2000 | Springer et al. |
| 6,017,696 | A | 1/2000 | Heller |
| 6,018,350 | A | 1/2000 | Lee et al. |
| 6,023,540 | A | 2/2000 | Walt et al. |
| 6,023,590 | A | 2/2000 | Abe et al. |
| 6,025,905 | A | 2/2000 | Sussman |
| 6,027,889 | A | 2/2000 | Barany et al. |
| 6,027,945 | A | 2/2000 | Smith et al. |
| 6,033,547 | A | 3/2000 | Trau et al. |
| 6,043,354 | A | 3/2000 | Hillebrand et al. |
| 6,048,690 | A | 4/2000 | Heller |
| 6,054,270 | A | 4/2000 | Southern |
| 6,060,243 | A | 5/2000 | Tang et al. |
| 6,063,569 | A | 5/2000 | Gildea et al. |
| 6,068,818 | A | 5/2000 | Ackley et al. |
| 6,075,905 | A | 6/2000 | Herman et al. |
| 6,077,669 | A | 6/2000 | Little et al. |
| 6,077,674 | A | 6/2000 | Schleifer et al. |
| 6,080,585 | A | 6/2000 | Southern et al. |
| 6,083,699 | A | 7/2000 | Leushner et al. |
| 6,083,763 | A | 7/2000 | Balch |
| 6,084,991 | A | 7/2000 | Sampas |
| 6,086,736 | A | 7/2000 | Dasgupta et al. |
| 6,090,458 | A | 7/2000 | Murakami |
| 6,090,545 | A | 7/2000 | Wohlstadter et al. |
| 6,090,555 | A | 7/2000 | Fiekowsky et al. |
| 6,090,912 | A | 7/2000 | Lebl et al. |
| 6,096,368 | A | 8/2000 | Sun |
| 6,100,030 | A | 8/2000 | McCasky Feazel et al. |
| 6,103,379 | A | 8/2000 | Margel et al. |
| 6,106,685 | A | 8/2000 | McBride et al. |
| 6,120,666 | A | 9/2000 | Jacobson et al. |
| 6,122,599 | A | 9/2000 | Mehta |
| 6,123,263 | A | 9/2000 | Feng |
| 6,124,092 | A | 9/2000 | O'Neill et al. |
| 6,126,731 | A | 10/2000 | Kemeny et al. |
| 6,130,101 | A | 10/2000 | Mao et al. |
| 6,132,685 | A | 10/2000 | Kercso et al. |
| 6,132,997 | A | 10/2000 | Shannon |
| 6,133,436 | A | 10/2000 | Koster et al. |
| 6,136,171 | A | 10/2000 | Frazier et al. |
| 6,136,468 | A | 10/2000 | Mitchell, Jr. et al. |
| 6,139,831 | A | 10/2000 | Shivashankar et al. |
| 6,141,046 | A | 10/2000 | Roth et al. |
| 6,143,499 | A | 11/2000 | Mirzabekov et al. |
| 6,149,789 | A | 11/2000 | Benecke et al. |
| 6,150,095 | A | 11/2000 | Southern et al. |
| 6,151,062 | A | 11/2000 | Inoguchi et al. |
| 6,153,375 | A | 11/2000 | Kobylecki et al. |
| 6,153,389 | A | 11/2000 | Haarer et al. |
| 6,156,502 | A | 12/2000 | Beattie |
| 6,167,910 | B1 | 1/2001 | Chow |
| 6,172,218 | B1 | 1/2001 | Brenner |
| 6,180,226 | B1 | 1/2001 | McArdle et al. |
| 6,183,970 | B1 | 2/2001 | Okano et al. |
| 6,187,540 | B1 | 2/2001 | Staub et al. |
| 6,193,866 | B1 | 2/2001 | Bader et al. |
| 6,193,951 | B1 | 2/2001 | Ottoboni et al. |
| 6,200,737 | B1 | 3/2001 | Walt et al. |
| 6,200,814 | B1 | 3/2001 | Malmqvist et al. |
| 6,203,993 | B1 | 3/2001 | Shuber et al. |
| 6,207,369 | B1 | 3/2001 | Wohlstadter et al. |
| 6,209,589 | B1 | 4/2001 | Hare et al. |
| 6,218,111 | B1 | 4/2001 | Southern et al. |
| 6,221,598 | B1 | 4/2001 | Schumm et al. |
| 6,232,066 | B1 | 5/2001 | Felder et al. |
| 6,235,471 | B1 | 5/2001 | Knapp et al. |
| 6,238,863 | B1 | 5/2001 | Schumm et al. |
| 6,245,508 | B1 | 6/2001 | Heller et al. |
| 6,251,592 | B1 | 6/2001 | Tang et al. |
| 6,251,595 | B1 | 6/2001 | Gordon et al. |
| 6,251,687 | B1 | 6/2001 | Buechler et al. |
| 6,251,691 | B1 | 6/2001 | Seul |
| 6,254,754 | B1 | 7/2001 | Ross et al. |
| 6,254,827 | B1 | 7/2001 | Ackley et al. |
| 6,261,430 | B1 | 7/2001 | Yager et al. |
| 6,261,782 | B1 | 7/2001 | Lizardi et al. |
| 6,264,815 | B1 | 7/2001 | Pethig et al. |
| 6,264,825 | B1 | 7/2001 | Blackburn et al. |
| 6,266,459 | B1 | 7/2001 | Walt et al. |
| 6,267,858 | B1 | 7/2001 | Parce et al. |
| 6,268,219 | B1 | 7/2001 | Mcbride et al. |
| 6,268,222 | B1 | 7/2001 | Chandler et al. |
| 6,271,856 | B1 | 8/2001 | Krishnamurthy |
| 6,277,579 | B1 | 8/2001 | Lazar et al. |
| 6,280,618 | B2 | 8/2001 | Watkins et al. |
| 6,287,778 | B1 | 9/2001 | Huang et al. |
| 6,294,063 | B1 | 9/2001 | Becker et al. |
| 6,297,062 | B1 | 10/2001 | Gombinski |
| 6,303,316 | B1 | 10/2001 | Kiel et al. |
| 6,306,643 | B1 | 10/2001 | Gentalen et al. |
| 6,307,039 | B1 | 10/2001 | Southern et al. |
| 6,309,602 | B1 | 10/2001 | Ackley et al. |
| 6,312,134 | B1 | 11/2001 | Jain et al. |
| 6,316,186 | B1 | 11/2001 | Ekins |
| 6,318,970 | B1 | 11/2001 | Backhouse |
| 6,319,472 | B1 | 11/2001 | Ackley et al. |

(56) References Cited

U.S. PATENT DOCUMENTS

| | | |
|---|---|---|
| 6,319,674 B1 | 11/2001 | Fulcrand et al. |
| 6,321,791 B1 | 11/2001 | Chow |
| 6,327,410 B1 | 12/2001 | Walt et al. |
| 6,342,355 B1 | 1/2002 | Hacia et al. |
| 6,349,144 B1 | 2/2002 | Shams |
| 6,355,419 B1 | 3/2002 | Alfenito |
| 6,355,431 B1 | 3/2002 | Chee et al. |
| 6,355,491 B1 | 3/2002 | Zhou et al. |
| 6,358,387 B1 | 3/2002 | Kopf-Sill et al. |
| 6,361,916 B1 | 3/2002 | Chen et al. |
| 6,361,945 B1 | 3/2002 | Becker et al. |
| 6,365,418 B1 | 4/2002 | Wagner et al. |
| 6,368,799 B1 | 4/2002 | Chee |
| 6,387,707 B1 | 5/2002 | Seul et al. |
| 6,399,328 B1 | 6/2002 | Vournakis et al. |
| 6,403,309 B1 | 6/2002 | Iris et al. |
| 6,406,921 B1 | 6/2002 | Wagner et al. |
| 6,426,615 B1 | 7/2002 | Mehta |
| 6,429,027 B1 | 8/2002 | Chee et al. |
| 6,448,012 B1 | 9/2002 | Schwartz |
| 6,451,191 B1 | 9/2002 | Bentsen et al. |
| 6,458,547 B1 | 10/2002 | Bryan et al. |
| 6,468,811 B1 | 10/2002 | Seul |
| 6,480,791 B1 | 11/2002 | Strathmann |
| 6,488,872 B1 | 12/2002 | Beebe et al. |
| 6,494,924 B1 | 12/2002 | Auweter et al. |
| 6,498,863 B1 | 12/2002 | Gaidoukevitch et al. |
| 6,500,620 B2 | 12/2002 | Yu et al. |
| 6,503,680 B1 | 1/2003 | Chen et al. |
| 6,506,564 B1 | 1/2003 | Mirkin et al. |
| 6,509,158 B1 | 1/2003 | Schwartz |
| 6,514,688 B2 | 2/2003 | Muller-Schulte |
| 6,514,714 B1 | 2/2003 | Lee et al. |
| 6,514,771 B1 | 2/2003 | Seul |
| 6,515,649 B1 | 2/2003 | Albert et al. |
| 6,521,747 B2 | 2/2003 | Anastasio et al. |
| 6,528,264 B1 | 3/2003 | Pal et al. |
| 6,531,292 B1 | 3/2003 | Rine et al. |
| 6,531,323 B1 | 3/2003 | Shinoki et al. |
| 6,534,274 B2 | 3/2003 | Becker et al. |
| 6,534,293 B1 | 3/2003 | Barany et al. |
| 6,540,895 B1 | 4/2003 | Spence et al. |
| 6,605,453 B2 | 8/2003 | Ozkan et al. |
| 6,605,474 B1 | 8/2003 | Cole |
| 6,610,256 B2 | 8/2003 | Schwartz |
| 6,620,584 B1 | 9/2003 | Chee et al. |
| 6,642,062 B2 | 11/2003 | Kauver et al. |
| 6,645,432 B1 | 11/2003 | Anderson et al. |
| 6,650,703 B1 | 11/2003 | Schwarzmann et al. |
| 6,670,128 B2 | 12/2003 | Smith et al. |
| 6,692,914 B1 | 2/2004 | Klaerner et al. |
| 6,703,288 B2 | 3/2004 | Nagasawa et al. |
| 6,706,163 B2 | 3/2004 | Seul et al. |
| 6,713,309 B1 | 3/2004 | Anderson et al. |
| 6,730,515 B2 | 5/2004 | Kocher |
| 6,743,581 B1 | 6/2004 | Vo-Dinh |
| 6,760,157 B1 | 7/2004 | Stover et al. |
| 6,779,559 B2 | 8/2004 | Parce et al. |
| 6,797,524 B1 | 9/2004 | Seul |
| 6,806,050 B2 | 10/2004 | Zhou et al. |
| 6,812,005 B2 | 11/2004 | Fan et al. |
| 6,838,289 B2 | 1/2005 | Bell et al. |
| 6,844,156 B2 | 1/2005 | Rosen |
| 6,869,798 B2 | 3/2005 | Crews et al. |
| 6,887,701 B2 | 5/2005 | Anderson et al. |
| 6,890,741 B2 | 5/2005 | Fan et al. |
| 6,897,271 B1 | 5/2005 | Domschke et al. |
| 6,905,881 B2 | 6/2005 | Sammak et al. |
| 6,908,737 B2 | 6/2005 | Ravkin et al. |
| 6,942,968 B1 | 9/2005 | Dickinson et al. |
| 6,955,751 B1 | 10/2005 | Seul |
| 6,955,889 B1 | 10/2005 | Mercolino et al. |
| 6,955,902 B2 | 10/2005 | Chumakov et al. |
| 6,958,245 B2 | 10/2005 | Seul et al. |
| 6,991,941 B1 | 1/2006 | Seul |
| 6,993,156 B1 | 1/2006 | Szeliski et al. |
| 7,015,047 B2 | 3/2006 | Huang et al. |
| 7,041,453 B2 | 5/2006 | Yang |
| 7,049,077 B2 | 5/2006 | Yang |
| 7,056,746 B2 | 6/2006 | Seul et al. |
| 7,060,431 B2 | 6/2006 | Chee et al. |
| 7,060,438 B1 * | 6/2006 | Mougin et al. ............... 435/6.12 |
| 7,090,759 B1 | 8/2006 | Seul |
| 7,097,974 B1 | 8/2006 | Stahler et al. |
| 7,099,777 B1 | 8/2006 | Ghandour |
| 7,115,884 B1 | 10/2006 | Walt et al. |
| 7,132,239 B2 | 11/2006 | Livak et al. |
| 7,141,217 B2 | 11/2006 | Karlsson et al. |
| 7,144,119 B2 | 12/2006 | Seul et al. |
| 7,157,228 B2 | 1/2007 | Hashmi et al. |
| 7,195,913 B2 | 3/2007 | Guire et al. |
| 7,229,840 B1 | 6/2007 | Wischerhoff |
| 7,262,016 B2 | 8/2007 | Huang et al. |
| 7,291,504 B2 | 11/2007 | Seul |
| 7,306,918 B2 | 12/2007 | Hashmi et al. |
| 7,320,864 B1 | 1/2008 | Yang |
| 7,335,153 B2 | 2/2008 | Seul et al. |
| 7,344,841 B2 | 3/2008 | Hashmi et al. |
| 7,358,097 B2 | 4/2008 | Seul et al. |
| 7,390,676 B2 | 6/2008 | Seul et al. |
| 7,425,416 B2 | 9/2008 | Hashmi et al. |
| 7,427,512 B2 | 9/2008 | Seul |
| 7,501,253 B2 | 3/2009 | Pourmand et al. |
| 7,526,114 B2 | 4/2009 | Xia et al. |
| 7,582,488 B2 | 9/2009 | Banerjee et al. |
| 7,595,279 B2 | 9/2009 | Wang et al. |
| 7,615,345 B2 | 11/2009 | Seul |
| 7,732,575 B2 | 6/2010 | Wang et al. |
| 7,737,088 B1 | 6/2010 | Stahler et al. |
| 7,749,774 B2 | 7/2010 | Seul |
| 7,790,380 B2 | 9/2010 | Yang |
| 7,848,889 B2 | 12/2010 | Xia et al. |
| 7,940,968 B2 | 5/2011 | Seul et al. |
| 2001/0034614 A1 | 10/2001 | Fletcher-Haynes et al. |
| 2001/0044531 A1 | 11/2001 | McGall et al. |
| 2001/0046602 A1 | 11/2001 | Chandler et al. |
| 2001/0049095 A1 | 12/2001 | Webster |
| 2002/0006634 A1 | 1/2002 | Han et al. |
| 2002/0015952 A1 | 2/2002 | Anderson et al. |
| 2002/0022276 A1 | 2/2002 | Zhou et al. |
| 2002/0029235 A1 | 3/2002 | Lock et al. |
| 2002/0031841 A1 | 3/2002 | Asher et al. |
| 2002/0032252 A1 | 3/2002 | Ishizuka |
| 2002/0039728 A1 | 4/2002 | Kain et al. |
| 2002/0045169 A1 | 4/2002 | Shoemaker et al. |
| 2002/0081714 A1 | 6/2002 | Jain et al. |
| 2002/0102567 A1 | 8/2002 | Fodor et al. |
| 2002/0125138 A1 | 9/2002 | Medoro |
| 2002/0127603 A1 | 9/2002 | Basiji et al. |
| 2002/0137074 A1 | 9/2002 | Piunno et al. |
| 2002/0142318 A1 | 10/2002 | Cattell et al. |
| 2002/0150909 A1 | 10/2002 | Stuelpnagel et al. |
| 2002/0155481 A1 | 10/2002 | Hirota et al. |
| 2002/0166766 A1 | 11/2002 | Seul et al. |
| 2002/0182609 A1 | 12/2002 | Arcot |
| 2002/0187501 A1 | 12/2002 | Huang et al. |
| 2002/0197728 A1 | 12/2002 | Kaufman et al. |
| 2002/0198665 A1 | 12/2002 | Seul et al. |
| 2003/0003272 A1 | 1/2003 | Laguitton |
| 2003/0004594 A1 | 1/2003 | Liu et al. |
| 2003/0006143 A1 | 1/2003 | Banerjee et al. |
| 2003/0012693 A1 | 1/2003 | Otillar et al. |
| 2003/0012699 A1 | 1/2003 | Moore et al. |
| 2003/0022370 A1 | 1/2003 | Casagrande et al. |
| 2003/0022393 A1 | 1/2003 | Seul et al. |
| 2003/0031351 A1 | 2/2003 | Yim |
| 2003/0038812 A1 | 2/2003 | Bartell |
| 2003/0040129 A1 | 2/2003 | Shah |
| 2003/0062422 A1 | 4/2003 | Fateley et al. |
| 2003/0077607 A1 | 4/2003 | Hopfinger et al. |
| 2003/0082487 A1 | 5/2003 | Burgess |
| 2003/0082530 A1 | 5/2003 | Soderlund et al. |
| 2003/0082531 A1 | 5/2003 | Soderlund et al. |
| 2003/0082587 A1 | 5/2003 | Seul et al. |

(56) References Cited

U.S. PATENT DOCUMENTS

| | | |
|---|---|---|
| 2003/0087228 A1 | 5/2003 | Bamdad et al. |
| 2003/0108913 A1 | 6/2003 | Schouten |
| 2003/0129296 A1 | 7/2003 | Kelso |
| 2003/0134326 A1 | 7/2003 | Hansen et al. |
| 2003/0138842 A1 | 7/2003 | Seul et al. |
| 2003/0148335 A1 | 8/2003 | Shen et al. |
| 2003/0152931 A1 | 8/2003 | Chiou et al. |
| 2003/0154108 A1 | 8/2003 | Fletcher-Haynes et al. |
| 2003/0177036 A1 | 9/2003 | Oka et al. |
| 2003/0182068 A1 | 9/2003 | Battersby et al. |
| 2003/0186220 A1 | 10/2003 | Zhou et al. |
| 2003/0228610 A1 | 12/2003 | Seul |
| 2004/0002073 A1 | 1/2004 | Li et al. |
| 2004/0009614 A1 | 1/2004 | Ahn et al. |
| 2004/0014073 A1 | 1/2004 | Trau et al. |
| 2004/0048259 A1 | 3/2004 | Hashmi et al. |
| 2004/0093238 A1 | 5/2004 | Deakter |
| 2004/0106121 A1 | 6/2004 | Ugolin et al. |
| 2004/0132122 A1 | 7/2004 | Banerjee et al. |
| 2004/0137641 A1 | 7/2004 | Holtlund et al. |
| 2004/0175734 A1 | 9/2004 | Stahler et al. |
| 2004/0219520 A1 | 11/2004 | Mirkin et al. |
| 2004/0229269 A1 | 11/2004 | Hashmi et al. |
| 2005/0048570 A1 | 3/2005 | Weber et al. |
| 2005/0112585 A1 | 5/2005 | Zichi et al. |
| 2005/0143928 A1 | 6/2005 | Moser et al. |
| 2005/0239098 A1 | 10/2005 | Hastings et al. |
| 2006/0024732 A1 | 2/2006 | Huang et al. |
| 2006/0035240 A1 | 2/2006 | Seul et al. |
| 2006/0275799 A1 | 12/2006 | Banerjee et al. |
| 2007/0031877 A1 | 2/2007 | Stahler et al. |
| 2007/0231810 A1 | 10/2007 | Todd et al. |
| 2007/0243534 A1 | 10/2007 | Seul et al. |
| 2008/0020374 A1 | 1/2008 | Greene et al. |
| 2008/0123089 A1 | 5/2008 | Seul et al. |
| 2008/0200349 A1 | 8/2008 | Wu et al. |
| 2008/0214412 A1 | 9/2008 | Stahler et al. |
| 2008/0261205 A1 | 10/2008 | Denomme |
| 2010/0062518 A1 | 3/2010 | Banerjee |

FOREIGN PATENT DOCUMENTS

| | | |
|---|---|---|
| EP | 0126450 | 11/1984 |
| EP | 179039 | 4/1986 |
| EP | 246864 | 11/1987 |
| EP | 269764 | 6/1988 |
| EP | 472990 | 3/1992 |
| EP | 478319 | 4/1992 |
| EP | 0529775 | 3/1993 |
| EP | 1394270 | 3/2004 |
| EP | 1564306 | 2/2005 |
| JP | 62265567 | 11/1987 |
| JP | 03-236777 | 10/1991 |
| WO | WO 8911101 | 5/1989 |
| WO | WO 9109141 | 6/1991 |
| WO | WO 9119023 | 12/1991 |
| WO | WO 9210092 | 6/1992 |
| WO | WO 9302360 | 2/1993 |
| WO | WO 9306121 | 4/1993 |
| WO | WO 9324517 | 12/1993 |
| WO | WO 9325563 | 12/1993 |
| WO | WO 9400810 | 1/1994 |
| WO | WO 9428028 | 9/1994 |
| WO | WO 9509248 | 4/1995 |
| WO | WO 9512608 | 5/1995 |
| WO | WO 9512808 | 5/1995 |
| WO | WO 9600148 | 1/1996 |
| WO | WO 9602558 | 2/1996 |
| WO | WO 9603212 | 2/1996 |
| WO | WO 9604547 | 2/1996 |
| WO | WO 9607917 | 3/1996 |
| WO | WO 9630392 | 10/1996 |
| WO | WO 9641011 | 12/1996 |
| WO | WO 9714028 | 4/1997 |
| WO | WO 9722720 | 6/1997 |
| WO | WO 9739151 | 10/1997 |
| WO | WO 9740383 | 10/1997 |
| WO | WO 9740385 | 10/1997 |
| WO | WO 9745559 | 12/1997 |
| WO | WO 9802752 | 1/1998 |
| WO | WO 9804950 | 2/1998 |
| WO | WO 9806007 | 2/1998 |
| WO | WO 9820153 | 5/1998 |
| WO | WO 9821593 | 5/1998 |
| WO | WO 9838334 | 9/1998 |
| WO | WO 9840726 | 9/1998 |
| WO | WO 9853093 | 11/1998 |
| WO | WO 9909217 | 2/1999 |
| WO | WO 9918434 | 4/1999 |
| WO | WO 9919515 | 4/1999 |
| WO | WO 9924822 | 5/1999 |
| WO | WO 9935499 | 7/1999 |
| WO | WO 9936564 | 7/1999 |
| WO | WO 9941273 | 8/1999 |
| WO | WO 9951773 | 10/1999 |
| WO | WO 9960170 | 11/1999 |
| WO | WO 9967641 | 12/1999 |
| WO | WO 0003004 | 1/2000 |
| WO | WO 0004372 | 1/2000 |
| WO | WO 0007019 | 2/2000 |
| WO | WO 0013004 | 3/2000 |
| WO | WO 0020593 | 4/2000 |
| WO | WO 0022172 | 4/2000 |
| WO | WO 0026920 | 5/2000 |
| WO | WO 0031356 | 6/2000 |
| WO | WO 0039587 | 7/2000 |
| WO | WO 00/47996 | 8/2000 |
| WO | WO 0046602 | 8/2000 |
| WO | WO 0051058 | 8/2000 |
| WO | WO 0062048 | 10/2000 |
| WO | WO 00/71750 * | 11/2000 ............... C12Q 1/68 |
| WO | WO 0073777 | 12/2000 |
| WO | WO 0075373 | 12/2000 |
| WO | WO 0101184 | 1/2001 |
| WO | WO 0120179 | 3/2001 |
| WO | WO 0136679 | 5/2001 |
| WO | WO 0154813 | 8/2001 |
| WO | WO 0156216 | 8/2001 |
| WO | WO 0184150 | 11/2001 |
| WO | WO 0188535 | 11/2001 |
| WO | WO 0194947 | 12/2001 |
| WO | WO 0198765 | 12/2001 |
| WO | WO 0212888 | 2/2002 |
| WO | WO 0214864 | 2/2002 |
| WO | WO 0231182 | 4/2002 |
| WO | WO 0233084 | 4/2002 |
| WO | WO 0235441 | 5/2002 |
| WO | WO 0237209 | 5/2002 |
| WO | WO 02057496 | 7/2002 |
| WO | WO 02058379 | 7/2002 |
| WO | WO 02061121 | 8/2002 |
| WO | WO 02079490 | 10/2002 |
| WO | WO 02084285 | 10/2002 |
| WO | WO 02096979 | 12/2002 |
| WO | WO 03020968 | 3/2003 |
| WO | WO 03025011 | 3/2003 |
| WO | WO 03034029 | 4/2003 |
| WO | WO 03058196 | 7/2003 |
| WO | WO 03079401 | 9/2003 |
| WO | WO 03092546 | 11/2003 |
| WO | WO 2004035426 | 4/2004 |
| WO | WO 2005000236 | 1/2005 |
| WO | WO 2005/045059 | 5/2005 |
| WO | WO 2005042763 | 5/2005 |
| WO | WO 2005045059 | 5/2005 |
| WO | WO 2005095650 | 10/2005 |
| WO | WO 2006/017473 | 2/2006 |
| WO | WO 2008040257 | 4/2008 |
| WO | WO 2009088893 | 7/2009 |
| WO | WO 2010025002 | 3/2010 |

(56) References Cited

FOREIGN PATENT DOCUMENTS

| WO | WO 2010026038 | 3/2010 |
|---|---|---|
| WO | WO 2010098765 | 9/2010 |
| WO | WO 2010143678 | 12/2010 |

OTHER PUBLICATIONS

Yeang et al. "Molecular Classification of multiple Tumor Types" *Bioinformatics* (2001) vol. 17, Suppl. 1 p. S316-S322.
Armstrong et al., "Suspension arrays for high throughput, multi-plexed single nucleotide polymorphism genotyping" Cytometry. vol. 40:102-108 (2000).
Bortolin, S. et al. "Analytical validation of the tag-it high-throughput microsphere-based universal arrray genotyping platform: application to the multiplex detection of a panel of thrombophilia-associated single-nucleotide polymorphisms" Clinical Chemistry, vol. 50 (11), pp. 2028-2036 (Sep. 13, 2004).
B.-Y. Ha et al., "Counterion-Mediated Attraction between Two Like-Charged Rods," Physical Review Letters, Aug. 18, 1997, vol. 79, No. 7, pp. 1289-1292.
A. Hatch, et al., "Diffusion Immunoassay in Polyacrylamide Hydrogels". Micro Total Analysis Systems, pp. 571-572 (2001).
Aho et al., "Efficient String Matching: An Aid to Bibliographic Search". Communications of the ACM, vol. 18, No. 6, pp. 333-340 (Jun. 1975).
Albergo et al., "Solvent effects on the thermodynamics of double-helix formation in (dG-sC) 3". Biochemistry, vol. 20, No. 6: 1413-1418 (1981).
Albrecht et al, "Probing the role of multicellular organization in three-dimensional microenvironments". Nature Methods, vol. 3, No. 5, pp. 369-375 (May 2006).
Albrecht et al., "Photo and electropatterning of hydrogel-encapsulated living cell arrays", Lab on a Chip, vol. 5, Issue 1, pp. 111-118 (2004).
Al-Soud, W. A., "Purification and Characterization of PCR-Inhibitory Components in Blood Cells", Journal of Clinical Microbiology, vol. 39, No. 2, pp. 485-493 (Feb. 2001).
Al-Soud, W. A., et al., "Identification and characterization of immunoglobulin G in blood as a major inhibitor of diagnostic PCR". Journal of Clinical Microbiology, vol. 38, No. 1, pp. 345-350 (Jan. 2000).
Ambruso, D. R., et al., "Experience with donors matched for minor blood group antigens in patients with sickle cell anemia who are receiving chronic transfusion therapy", Transfusion, vol. 27, No. 1, 1987, pp. 94-98.
Zhang, Y., et al., "Reproducible and inexpensive probe preparation for oligonucleotide arrays". Nucleic Acids Research, vol. 29, No. 13, pp. E66-6 (Jul. 1, 2001).
Arenko, et al., "Protein microchips: Use for immunoassay and enzymatic reactions". Analytical Biochemistry, vol. 278, pp. 123-131 (2000).
Assie et al., Correlation between low/high affinity ratios for 5-HT Receptors and Intrinsic Activity, European Journal of Pharmacology, vol. 386, pp. 97-103 (1999).
Bakewell et al., "Characterization of the dielectrophoretic movement of DNA in micro-fabricated structures", Institute of Physics Conference Series (1999) Electrostatics (1999).
Balass et al. "Recovery of high-affinity phage from a Nitrostretavidin matrix in phage-display technology". Analytical Biochemistry. vol. 243: 264-269 (1996).
Baldwin, E., "Phosphorylation of gastrin-17 by epidermal growth factor-stimulated tyrosine kinase". Nature, vol. 44, pp. 2403-2404 (1998).
Bandeira-Melo, C., et al., "EliCell: A gel-phase dual antibody capture and detection assay to measure cytokine release from eosinophils". Journal of Immunological Methods, vol. 244, pp. 105-115 (2000).
Bao, Y. P., et al., "Detection of Protein Analytes via Nanoparticle-Based Bio Bar Code Technology". Anal. Chem., vol. 78, pp. 2055-2059 (2006).

Barany, Francis, "Genetic Disease Detection and DNA Amplification using Cloned Thermostable Ligase". Proceedings of the National Academy of Sciences of the United States of America, vol. 88, pp. 189-193 (Jan. 1991).
Barnard et al. "A fibre-optic chemical sensor with descrete sensing sites". Nature, vol. 353:338-340 (1991).
Basu, S., et al., "Synthesis and Characterization of a Peptide Nucleic Acid Conjugated to a D-Peptide Analog of Insulin-like Growth Factor 1 for Increased Cellular Uptake". Bioconjugate Chem, vol. 8, No. 4, pp. 481-488 (1997).
Battersby et al., "Toward Larger Chemical Libraries: Encoding with Fluorescent Colloids in Combinatorial Chemistry". J. Amer Chem Soc, vol. 122, pp. 2138-2139 (2000).
Baumgarth N. et al., A practical approach to multicolor flow cytometry for immunophenotyping, J. Immunological Methods, 2000, pp. 77-97, vol. 243.
Bavykin, S.G., et al., "Portable system for microbial sample preparation and oligonucleotide microarray analysis". Appl. Environmental Microbiol. 67(2), 922-928 (2001).
Beatty et al. "Probability of Finding HLA-mismatched Related or Unrelated Marrow or Cord Blood Donors", Human Immunology, 2001, vol. 61, pp. 834-840.
Beebe et al., "Functional Hydrogel structures for autonomous flow control inside microfluidic channels". Nature, vol. 404, No. 6778, pp. 588-590 (Apr. 6, 2000).
Beiboer, S. W., et al., "Rapid genotyping of blood group antigens by multiplex polymerase chain reaction and DNA microarray hybridization" 45 Transfusion 667-679 (2005).
Bennett, P. R., et al., "Prenatal Determination of Fetal RhD Type by DNA Amplification". The New England Journal of Medicine, vol. 329, No. 9, pp. 607-610 (Aug. 26, 1993).
Bernard, Philip S., "Homogenous Multiplex Genotyping of Hemochromatasis Mutations with Fluorescent Hybridization Probes". American Journal of Pthology, vol. 153, No. 4, pp. 1055-1061 (1998).
Bessetti, J., "An introduction to PCT Inhibitors". Profiles in DNA-PCR Inhibition, pp. 9-10 (Mar. 2007).
Bickel, P. J., "Discussion of the Evaluation of Forensic DNA Evidence". Proc. Natl. Acad. Sci., vol. 94, p. 5497 (May 1997).
Zhang, X., et al., "Strand invasion by mixed base PNAs and a PNA-peptide chimera". Nucleic Acids Research, vol. 28, No. 17, pp. 3332-3338 (2000).
Blaaderen, et al., "Synthesis and Characterization of Colloidal Dispersions of Fluorescent, Monodisperse Silica Spheres". Langmuir, vol. 8, No. 2, pp. 2921-2931 (1992).
Bonnet, G., et al., "Thermodynamic basis of the enhanced specificity of structured DNA probes," Proc. Natl. Acad. Science, USA, vol. 96, pp. 6171-6176, May 1999.
Bos et al., "Controlled release of pharmaceutical protein from hydrogels". Business Briefing: Pharmatech, pp. 184-187 (2002).
Boyce, et al. "Peptidosteroidal Receptors for Opioid Peptides. Sequence-Selective Binding Using a Synthetic Receptor Library". J. Am. Chem. Soc., vol. 116, No. 17, pp. 7955-7956 (1994).
Boyd et al., "Tosyl Chloride activation of a rayon/polyester cloth for protein immobilization", Biotechnology Techniques, Apr. 1993, vol. 7, 4:277-282.
Braga et al., "Hydrophobic Polymer Modification with Ionic Reagents: Polysterene Staining with Water-Soluble Dyes". Langmuir, vol. 19, No. 18, pp. 7580-7586 (2003).
Breslauer, K.J. et al., "Predicting DNA duplex stability from the base sequence". PNAS USA, vol. 83, pp. 3746-3750 (1986).
Brick, et al., "Formation of Colloidal Dispersions of Organic Materials in Aqueous Media by Solvent Shifting". Langmuir, vol. 19, No. 16, pp. 6367-6380 (Jan. 31, 2003).
Broude et al., "Multiplex allele-specific target amplification based on PCR suppression". PNAS. vol. 98, No. 1, pp. 206-211 (2001).
Brown, Patrick O., et al., "Exploring the new world of the genome with DNA microarrays". Nature Genetics Supplement, vol. 21, pp. 33-37 (Jan. 1999).
Buck et al., "Design Strategies and Performance of Custom DNA Sequence Primers". BioTechniques, vol. 27, pp. 528-536 (Sep. 1999).

(56) References Cited

OTHER PUBLICATIONS

Bunce et al., "Phototyping: Comprehensive DNA Typing for HLA-A, B, C, DRB1, DRB2, DRB3, DRB4, DRB5 & DQB1 by PCR with 144 primer mixes utilizing sequence-specific primers (PCR-SSP)". Tissue Antigens, vol. 46, No. 5, pp. 355-367 (Nov. 1995).
Bunce, M., et al., "Comprehensive serologically equivalent DNA typing for HLA-A by PCR using sequence specific primers (PCR_SSP)", Tissue Anitigens 45 : 81-90 (1995).
Burbulis, I, et al., "Using protein-DNA chimeras to detect and count small numbers of molecules". Nature Methods, vol. 2, No. 1, pp. 31-37 (Jan. 2005).
Cai et al., "Flow cytometry-based minisequencing: A new platform for high-throughput throughput single-nucleotide polymorphism scoring", Genomics 66:135-143 (2000).
Campbell, C. J., et al., "Cell Interaction Microarray for Blood Phenotyping". Analytical Chemistry, vol. 78, pp. 1930-1938 (2006).
Campian et al. Colored and fluorescent solid supports. Innovation and Perspectives in Solid Phase Synthesis. Ed: E. Birmingham (Mayflower, London), pp. 469-474 (1994).
Cao et al., "High and intermediate resolution DNA typing systems for class I HLA-A, B, C genes by hybridization with sequence-specific oligonnucleotide probes (SSOP)", Rev Immunogenetics 1:177-208 (1999).
Cao et al., "Nanoparticles with Raman Spectroscopic Fingerprints for DNA and RNA Detection", Science 197:1536-1539 (2002).
Caruso et al., "Magnetic Core-Shell Particles: Preparation of Magnetite Multilayers on Polymer Latex Microspheres". Advanced materials, vol. 11, No. 11, pp. 950-953 (1999).
Caruso, et al., "Magnetic Nanocomposite Particles and Hollow Spheres Constructed by a Sequential Layering Approach". Chem Mater, vol. 13, No. 1, pp. 109-116 (2001).
Caruso. "Nanoengineering of Particle Surfaces". Advanced Materials, vol. 12, No. 1, pp. 11-22 (2001).
Casnellie JE, et al., "Phosphorylation of synthetic peptides by a tyrosine protein kinase from the particulate fraction of a lymphoma cell line". Proc natl Sci USA, vol. 79, No. 2, pp. 282-286 (1982).
Chalmers, et al., "An instrument to determine the magnetophoretic mobility of labeled, biological cells and paramagnetic particles". Journal of Magnetism and Magnetic Materials, vol. 194, pp. 231-241 (1999).
Chan et al. The Bipohysics of DNA Hybridization with Immobilized Oligonucleotide Probes. Biophysical Journal 69: pp. 2243-2255 (1995).
Chang, et al., "New Approach to Produce monosized Polymer Microcapsules by the Solute Co-diffusion Method". Langmuir, vol. 17, No. 18, pp. 5435-5439 (2001).
Zhang et al., "Reconstruction of DNA sequencing by hybridization". Bioinformatics, vol. 19, No. 1, pp. 14-21 (2003).
Chaudhry et al., "Reactivity of human apurinic/apyrimidinic endonuclease and *Escheria coli* exonucleonase III with bistranded abasic sites in DNA". The Journal of Biological Chemisty., vol. 272: 15650-15655 (1997).
Chee, M. et al., "Accessing genetic information with high-density DNA arrays". Science, vol. 274, pp. 610-613 (1996).
Chen et al., "A Microsphere-Based assay for multiplexed single nucleotide polymorphism analysis using single base chain extension", Genome Research, Cold Spring Harbor Laboratory Press 10:549-557 (2000).
Zhang et al., "Nuclear DNA analysis in genetic studies of populations; practice, problems and prospects" Molecular Ecology. vol. 12:563-584 (2003).
Chen, YX, et al., "Deletion of arginine codon 229 in the Rhce gene alters e and f but not c antigen expression". vol. 44, No. 3, pp. 391-398 (Mar. 2004).
Cheng, et al., "A Synthetic peptide derived from p34cdc2 is a Specific and Efficient Substrate of SRC-Family Tyrosine Kinases". J Biol Chem, pp. 9248-9256. vol. 267, No. 13 (1992).
Zborowski, et al., "Continuous cell separation using novel magnetic quadruple flow sorter". Journal of Magnetism and Magnetic Materials, vol. 194, pp. 224-230 (1999).

Cherepinsky, Vera, "On mathematical aspects of genomic analysis", Ph.D. Thesis, published Mar. 2004.
Cheung, V. G., et al., "Making and Reading Microarrays". vol. 21, pp. 15-19 (Jan. 1999).
Choi, et al., "An on-chip magnetic separator using spiral electromagnets with semi-encapsulated permalloy". Biosensors & Bioelectronics, vol. 16, pp. 409-416 (2001).
Yellen, B. B., et al., "Programmable Assembly of Colloidal Particles Using Magnetic Microwell Templates". Langmuir, p. est 6.5 (2004).
Clerc, P., et al., "Advanced deep reactive ion etching: a versatile tool for microelectromechanical systems". J. Micromech Microeng, vol. 8, No. 4, pp. 272-278 (Dec. 1998).
Coffer et al., "Characterization of Quantum-Confined CdS Nanocrystallites Stabilized by Deoxyribonucleic Acid (DNA)" Nanotechnology, 1992 3:69-75.
Yeh, S. R., et al., "Assembly of ordered colloidal aggregares by electric-field-induced fluid flow". Nature, Mar. 6, 1997; vol. 386, No. 6620, pp. 57-59.
Colombie, et al., "Role of Mixed Anionic-Nonionic Systems of Surfactants in the Emulsion Polymerization of Styrene: Effect on Particle Nucleation". Macromolocules, vol. 33, No. 20, pp. 7283-7291 (2000).
Cosgrove et al. "A Small-angle neutron scattering study of the structure of gelatin at the surface of polystyrene latex particles". Langmuir. vol. 14:5376-5382 (1998).
Coyne et al., "Assymetric PCR for ssDNA Production", Molecular Biology Techniques Manual. Third Edition. Jan. 1994, Feb. 2001; http://www.mcb.uct.ac.za/pcrcond.htm.
Crisp, M., et al., "Preparation of Nanoparticle Coatings on Surfaces of Complex Geometry". Nano Letters, vol. 3, No. 2, pp. 173-177 (2003).
Cronin M.T. et al., "Cystic Fibrosis Mutation Detection by Hybridization to Light-Generated DNA Probe Arrays," Human Mutation, John Wiley & Sons, Inc., US, vol. 7, No. 3, pp. 244-255 (Jan. 1996).
Cruse et al., "Illustrated Dictionary of Immunology". Boca Raton: CRC Press, p. 512 (2003).
Dai-Wu Seol, et al., "Signaling Events Triggered by Tumor Necrosis Factor-related Apoptosis-inducing Ligand (TRAIL): Caspase-8 is Required for TRAIL-Induced Apoptosis". Cancer Research, vol. 61, pp. 1138-1143 (2001).
Dasgupta, et al., "Flow of multiple fluids in a smalll dimension". Analytical Chemistry, vol. 74, No. 7, pp. 208-213 (2002).
De Farias, P., et al., Investigation of red blood cell antigens with highly fluorescent and stable semiconductor quantum dots, J. Bimedical Optics, 2005, pp. 1-4, vol. 10(4).
Decher, G., "Fuzzy Nanoassemblies: Toward Layered Polymeric Multicomposites". Science, vol. 277, pp. 1232-1237 (Aug. 29, 1997).
Denomme, G. A., et al., "High throughput multiplex single-nucloetide polymorphism analysis for red cell and platelet antigen genotypes". Transfusion, vol. 45, pp. 660-666 (May 2005).
Denkov et al. "Mechanism of Formation of Two-Dimensional Crystals from Latex Particles on Substrates," langmuir, 1992, pp. 3183-3190, vol. 8.
Ding et al., "Direct molecular haplotyping of long-range genomic DNA with M1-PCR", Jun. 2003, vol. 100, 13: 7449-7453.
Du et al., "Sensitivity and Specificity of Metal Surface-Immobilized," Molecular Beacon, Biosensors; JACS 2005, vol. 127, No. 21, pp. 7932-7940.
Duggan, David J., et al., "Expression profiling using cDNA microarrays". Nature Genetics Supplement, vol. 21, pp. 10-14 (Jan. 1999).
Dunbar SA et al. "Application of the luminex LabMAP in rapid screening for mutations in the cystic fibrosis transmembrane conductance regulator gene: A pilot study" Clin Chem Sep. 2000; 46(9): 1498-500. with Abstract data, pp. 1 and 2.
Duquesnoy HLA Matchmaker: A Molecularly Based Algorithm for Histocompatibility Determination. I. Description of the Algorithm. Human Immunology, vol. 63, pp. 339-352 (2002).
Dziennik, S. R., et al., "Nondiffusive mechanisms enhance protein uptake rates in ion exchange particles". PNAS, vol. 100, No. 2, pp. 420-425 (2003).
Easteal, S. "DNA Fingerprinting by PCR Amplification of HLA Genes". DNA and Criminal Justice; Human Genetics Group, John Curtin School of Medical Research, pp. 121-127 (1991).

(56) References Cited

OTHER PUBLICATIONS

Egner et al. "Tagging in combinatorial chemistry: the use of coloured and fluorescent beads". Chem. Commun. pp. 735-736 (1997).
Elaissari et al., "Hydrophilic and cationic latex particles for the specific extraction of nucleic acids". J. Biomater, Sci Polymer Edn, vol. 10, pp. 403-420 (1999).
Erdogan et al., "Detection of mitochondrial single nucleotide polymorphisms using a primer elongation reaction on oligonucleotide microarrays", Nucleic Acid Research, 29 : 1-7 (2001).
Ericsson, O., et al., "A dual-tag microarray platform for high-performance nucleic acid and protein analyses". Nucleic Acids Research, vol. 36, No. 8 e45, pp. 1-9 (2008).
Erlich, et al., "HLA DNA Typing and Transplantation", Immunity, 14: 347-356 (2001).
Fan et al., "Parallel Genotyping of Human SNPs Using Generic High-density Oligonucleotide Tag Arrays", Genome Research, vol. 10, pp. 853-860 (2000).
Fatin-Rouge, N., et al., "Diffusion and Partitioning of Solutes in Agarose Hydrogels: The Relative Influence of Electrostatic and Specific Interactions", J. Phys. Chem. B., vol. 107, pp. 12126-12137 (2003).
Ferguson et al., "High-Density Fiber-Optic DNA Random Microsphere Array". Anal. Chem, vol. 72, pp. 5618-5624 (2000).
Filipovich et al., "Impact of donor type on outcome of bone marrow transplantation for Wiskott-Aldrich syndrome: collaborative study of the International Bone Marrow Transplant Registry and the National Marrow Donor Program", Blood, vol. 97, No. 6, pp. 1598-1603 (2001).
Finkel, et al. "Barcoding the Microworld". Analytical Chemistry, pp. 353-359 (Oct. 1, 2004).
Fitch, J.P. et al., "Rapid Development of Nucleic Acid Diagnostics", Proceedings of the IEEE 90 (11): 1708-1720 (Nov. 2002).
Fluorescent Microspheres (Tech. Note #19). Bangs Laboratories (1997).
Fodor, S., et al., "Light-Directed, Spatially Addressable Parallel Chemical Synthesis". Research Article (Authors are at the Affymax Research Institute, 3180 Porter Drive, Palo Alto, CA 94304), pp. 767-773 (Feb. 15, 1991).
Fowke, Keith R., et al. "Genetic analysis of human DNA recovered from minute amounts of serum or plasma". Journal of Immunological Methods, vol. 80, pp. 45-51 (1995).
Frengen, Jomar, et al., "Demonstration and Minimization of Serum Interference in Flow Cytometric Two-Site Immunoassays". Clinical Chemistry, vol. 40, No. 3, pp. 420-425 (1994).
Fuh et al. Single Fibre Optic Fluorescence pH Probe. Analyst, 112:1159-1163 (1987).
Fuh et al., "A Method for Determination of Particle Magnetic Susceptibility with Analytical Magnetapheresis". Anal. Chem, vol. 72, pp. 3590-3595 (2000).
Fulton et al. "Advanced multiplexed analysis with the FlowMetrix system". Clinical Chemistry, vol. 43:9, pp. 1749-1756 (1997).
Gahan, P. B., "Circulating Nucleic Acid in Plasma and Serum: Diagnosis and Prognosis in Cancer". Oncology, vol. 32, No. 6, pp. 20-22 (Oct. 2008); Weekly news updates on www.cli-online.com.
Garber, K. "More SNPs on the Way". Science, vol. 281, No. 5384, pp. 1788-1790 (Sep. 18, 1998).
Gates, et al., "Photonic Crystals that can be Addressed with an External Magnetic Field". Adv Mater, vol. 13, No. 21, pp. 1605-1608 (2001).
Gelfi, C., et al., "Investigation of the Properties of Novel Acrylamido Monomers by Capilary Zone Electrophoresis", Journal of Chromatography, vol. 608, pp. 333-341 (1992).
Gerlach. Human Lymphocyte Antigen Molecular Typing. Archives of Pathology & Laboratory Medicine. vol. 126, pp. 281-284 (2002).
Ghazaly, et al., "Synthesis and Characterization of a Macromonomer Crosslinker". Journal of Applied Polymer Science, vol. 77, pp. 1362-1368 (2000).

Ghosh et al. "Covalent attachement of oligonucleotides to solid supports". Nucleic Acids Research. vol. 16, No. 13; pp. 5363-5371 (1987).
Ghosh, P., et al., "A Simple Lithographic Approach for Preparing Patterned, Micron-Scale Corrals for Controlling Cell Growth". Angew. Chem. Int. Ed., vol. 38, No. 11, pp. 1592-1595 (1999).
Giersig et al. Formation of ordered two-dimensional gold colloid lattices by electrophoretic deposition. J. Phys. Chem., vol. 97: 6334-6336 (Apr. 29, 1993).
Giorgi, R., et al., "Nanotechnologies for Conservation of Cultural Heritage: Paper and Canvas Deacidification". Langmuir, vol. 18, pp. 8198-8203 (2002).
Good, L., et al., "Bactericidal antisense effects of peptide-DNA conjugates". Nature Biotechnology, vol. 19, pp. 360-364 (2001).
Goodey et al., "Development of multianalyte sensor arrays composed of chemically derivatized polymeric microspheres localized in micromachined cavitites". Journal of American Chemical Society, vol. 123, pp. 2559-2570 (2001).
Graf et al., "A general method to coat colloidal particles with silica". Langmuir, vol. 19, pp. 6693-6700 (2003).
Grazia et al. In-vivo biomedical monitoring by fiber-optic system. Journal of Lightwave Technology. 13, 1396-1406 (1995).
Yellen, et al., "Statistical Analysis of Weakest Link in Chains of Magnetic Particle Carriers for Applications in Printing Biochemical Arrays". European Cells and Materials, vol. 3, pp. 88-91 (2002).
Grondahl, et al., "Encoding Combinatorial Libraries: A Novel Application of Fluorescent Silica Colloids". Langmuir, vol. 16, No. 25, pp. 9709-9715 (2000).
Gruttner, et al,, "New types of silica-fortified magnetic nanoparticles as tools for molecular biology applications". Journal of Magnetism and Magnetic Materials, vol. 94, pp. 8-15 (1999).
Gubin et al., "Identification of the Dombrock blood group glycoprotein as a polymorphic member of the ADP-ribosyltransferase gene family", Blood, Oct. 1, 2000, vol. 96, No. 7, pp. 2621-2627.
Gullberg, M., et al., "Cytokine detection by antibody-based proximity ligation". PNAS, vol. 101, No. 22, pp. 8420-8424 (Jun. 2004).
Guo, Zhen et al. "Oligonucleotide arrays for high-throughput SNPs detection in the MHC class I genes: HLA-B as a model system". Genome Research; vol. 12, No. 3, pp. 447-457 (Mar. 2002).
Guo, Zhen, "Direct fluorescence analysis of genetic polymorphisms . . . oligonucleotide arrays on glass supports". Nucleic Acids Research, Jul. 1994, Oxford Univ Press, pp. 5456-5465.
Gupta et al. ("Hydrogels: from controlled release to pH-responsive drug delivery" Drug Discov Today. May 15, 2002;7(10):569-79.
Gustafsdottir, S. M., "In vitro analysis of DNA-protein interactions by proximity ligation". PNAS, vol. 104, No. 9, pp. 3067-3072 (Feb. 2007).
Haab et al. Single Molecule Fluorescence Burst Detection of DNA Fragments Separated by Capillary Electrophoresis. Analytical Chemistry, vol. 67 (No. 18) : 3253-3256 (1995).
Hacis et al., "Resequencing and mutational analysis using oligonucleotide microarrays", Nature America; 21 : 42-47 (1999).
Hakala, H., et al. "Simultaneous detection of several oligonucleotides by time-resolved fluorometry: the use of a mixture of categorized microparticles in a sandwich type mixed-phase hybridization assay". Nucleic Acids Research, vol. 26, pp. 5581-5585 (1998).
Hashimi et al., "A Flexible Array format for large-scale, rapid blood group DNA typing". Transfusion, Published Online Apr. 6, 2004, vol. 45, Issue 5, pp. 680-688 (May 2005).
Hashmi, G., et al, "Determination of 24 minor red blood cell antigens for more than 2000 blood donors by high-throughput DNA analysis". Transfusion, vol. 47, No. 4, pp. 736-747 (Apr. 2007).
Zaer, Farid, et al., "Antibody Screening by Enzyme-Linked Immunosorbent Assay Using Pooled Soluble HLA in Renal Transplant Candidates", Transplantation, vol. 63, No. 1, pp. 48-51 (Jan. 15, 1997).
Heinrich, et al., "Interleukin-6-type Cytokine Signaling through the gp 130/Jak/STAT pathway". Biochem J, vol. 334, pp. 297-314 (1998).

(56) References Cited

OTHER PUBLICATIONS

Helgesen, et al., "Aggregation of magnetic microspheres: experiements and simulations". Physical Review Letters, vol. 61, No. 15, pp. 1736-1739 (1998).
Helmuth, R., et al., "HLA-DQ Allele and Genotype Frequencies in Various Human Populations, Determined by Using Enzymatic Amplification and Oligonucleotide Probes". Am. J. Hum. Genet, vol. 47, pp. 515-523 (1990).
Hermanson, G. T., "Nucleic Acid and Oligonucleotide Modification and Conjugation". Bioconjugate Techniques, Academic Press, Chapter 17, pp. 639-671 (Jan. 15, 1996).
Yershov et al., "DNA analysis and diagnostics on oligonulceotide microchips". Proceedings of the National Academy of Sciences of the United States of America, vol. 93, No. 10, pp. 4913-4918 (May 14, 1996).
Hiller, J., et al., "Reversibly erasable nanoporous anti-reflection coatings from polyelectrolyte multilayers". Nature Materials, vol. 1, pp. 59-63 (Sep. 2002).
Hirata, H., et al., "Caspases Are Activated in a Branched Protease Cascade and Control Distinct Downstream Processes in Fas-induced Apoptosis". J. Exp. Med., vol. 187, No. 4, pp. 587-600 (1998).
Hizume, et al., "Tandem repeat DNA localizing on the proximal DAPI bands of chromosomes in Larix, pinaceae". Genome, vol. 45, pp. 777-783 (2002).
Holtz, J., et al., "Intelligent Polymerized Crystalline Colloidal Array: Novel Sensor Materials", Analytical Chemistry, vol. 70, No. 4, pp. 780-791 (1998).
Houghton. "General method for the rapid solid-phase synthesis of large numbers of peptides: specificity of anitgen-antibody interaction at the level of individual amino acids". Proc. Natl. Avad. Sci. USA. vol. 82:5131-5135 (1985).
Huff et al., "Technical Milestone: Development of the Logical Obervation Identifier Names and Codes (LOINC) Vocabulary". JAIMA, vol. 5, pp. 276-292 (1998).
Iannone, Marie A., et al., "Multiplexed Single Nucelotide Polymorphism Genotyping by Oligonucleotide Ligation and Flow Cytometry". Cytometry, vol. 39, Issue 2, pp. 131-140 (Feb. 17, 2000).
Ide et al., "Synthesis and damage specificity of a novel probe for the detection of abasic sites in DNA". Biochemistry. vol. 32: 8276-8283 (1993).
Ito, Y., et al., "Patterned Immobilization of Thermoresponsive Polymer", Langmuir, vol. 13, pp. 2756-2759 (1997).
Iwayama, et al., "Optically Tunable Gelled Photonic Crystal Covering Almost the Entire Visible Light Wavelength Region", Langmuir (2002).
Jackman, R. J., et al., "Using Elastomeric Membranes as Dry Resists and for Dry Lift-Off", Langmuir, vol. 15, pp. 2973-2984 (1999).
Jeon, N. L., et al., "Patterned polymer growth on silicon surfaces using microcontact printing and surface-initiated polymerization", Applied Physics Letters, vol. 75, No. 26, pp. 4201-4203 (1999).
John C. Guatelli et al., "Isothermal, in vitro amplification of nucleic acids by a multienzyme reaction modeled after retroviral replication," Proc. Nat'l Academy of Science USA, vol. 87: pp. 1874-1878 (1990).
Johnson, K. L., et al., "Surface Energy and the Contact of Elastic Solids". Proceedings of the Royal Society of London, Series A, Mathematical and Physical Sciences, vol. 324, No. 1558, pp. 301-313 (Sep. 8, 1971).
Jones et al., "Constraint, Optimization, and Hierarchy: Reviewing Stereoscopic Correspondence of Complex Features". Computer Vision and Image Understanding, vol. 65, No. 1, pp. 57-78 (1997).
Jones et al., "Dielectrophoretic liquid actuation and nanodroplet formation", Journal of Applied Physics, vol. 89, No. 2, pp. 1441-1448 (Jan. 15, 2001).
Kakabakos et al. "Immobilization of Immunoglobulins onto Surface-treated and Untreated Polystyrene Beads for Radioimmunoassays" Clin. Chem. 36 (1990), 492-496.
Kalinina, O., et al., "A core-shell Approach to Producing 3D Polymer Nanocomposites", Macromolecules, vol. 32, pp. 4122-4129 (1999).

Kamholz, et al., "Optical measurement of transverse molecular diffusion in a microchannel". Biophysical Journal, vol. 80, pp. 1967-1972 (2001).
Kamm, R. C., et al. "Nucleic Acid Concentrations in Normal Human Plasma". Clinical Chemistry, vol. 18, pp. 519-522 (1972).
Kandimalla et al., "Cyclicons" as Hybridization-Based Fluorescent Primer-Probes: Bioorganic & Medicinal Chemistry 8 (2000) 1911 to 1916.
Kelly, J.J., et al., "Radical-generating coordination complexes as tools for rapid and effective fragmentation and fluorescent labeling of nucleic acids for microchip hybridization". Analytical Biochemisty, vol. 311, No. 2, pp. 103-118 (Dec. 15, 2002).
Klintschar, et al., "Genetic variation at the STR loci D12S391 and CSF1PO in four populations from Austria, Italy, Egypt and Yemen". Forensic Sci. Int. vol. 97:37-45 (1998).
Kim, E., et al., "Polymer microstructures formed by moulding in capillaries", Nature, vol. 376, pp. 581-584 (1995).
Knipper, et al., Accession No. AF221125.1.1 on Electronic Database at NCBI (Feb. 16, 2000).
Koch et al., "PNA-Peptide Chimerae". Tetrahedron Letters, vol. 36, pp. 6933-6936 (1995).
Koh, et al., "Molding of Hydrogel Microstructures to Create Multiphenotype Cell Microarrays". Analytical Chemistry (2003).
Koh, et al., "Poly(ethylene glycol) Hydrogel Microstructures Encapsulating Living Cells". Langmuir, vol. 18, pp. 2459-2462 (2002).
Kolch. "Meaningful Relationships: The Regulation of the Ras/Raf/MEK/ERK pathway by protein interactions". Biochem J, vol. 351, pp. 289-305 (2000).
Kotov, N., et al., "Layer-by-Layer Self-Assembly of Polyelectrolyte-Semicondictor Nanoparticle Composite Films". J. Phy Chem, vol. 99, pp. 13065-13069 (1995).
Krause et al. "A Comprehensive PCR-ssP typing system for identification of HLA-A locus alleles", Tissue Antigens, 47 (3) : 237-244 (1996).
Krsko, P., et al., "Electron-Beam Surface Patterned Poly(ethylene glycol) Microhydrogels". Langmuir, vol. 19, pp. 5618-5625 (2003).
Krutzik P.O. et al., "Fluorescent cell barcoding in flow cytometry allows high-throughput drug screening and signal profiling". Nature Methods, vol. 3, No. 5, pp. 361-368 (2006).
Kubo et al., "A Novel Sensitive and specific assay for abasic sites, the most commonly produced DNA lesion". Biochemistry, vol. 13:3703-3708 (1992).
Kumacheva, E., et al., "Three-dimensional Arrays in Polymer Nanocompositites", Advanced Materials, vol. 11, No. 3, pp. 231-234 (1999).
Kurita-Ochiai, T., et al., "Butyric Acid-Induced T-Cell Apoptosis is Mediated by Caspase-8 and -9 Activation in a Fas-Independent Manner". Clinical and Diagnostic Laboratory Immunology, vol. 8, No. 2, pp. 325-332 (2001).
Vorlop, K. D., et al., "Entrapment of Microbial Cells within Polyurethane Hydrogel Beads with the Advantage of Low Toxicity", Biotechnology Techniques, vol. 6, No. 6, pp. 483-488 (1992).
Kwoh et al., "Transcription based amplification system and detection of amplified human immunodeficiency virus type 1 with a bead-based sandwich hybridization format". Proc. Natl. Acad. Sci, vol. 86, pp. 1173-1177 (Feb. 1989).
LaForge, K. S., et al., "Detection of Single Nucleotide Polymorphisms of the Human Mu Opioid Receptor Gene by Hybridization of Single Nucleotide Extension on Custom Oligonucleotide Gelpad Microchips: Potential in Studies of Addiction". American Journal of Medical Genetics (Neuropsychiatric Genetics), vol. 96, pp. 604-615 (2000).
Lagerholm et al., "Theory for Ligand Rebinding at Cell Membrane Surfaces," Biophysical Journal (1998), vol. 74, pp. 1215-1228.
Lamb, D. J., et al., "Modification of Natural and Artificial Polymer Colloids by Topology-Controlled Emulsion Polymerization". Biomacromolecules, vol. 2, No. 2, pp. 518-525 (2001).
Lander, E. S. "The New Genomics: Global Views of Biology". Sciences, vol. 274, No. 5287, pp. 536-539 (Oct. 25, 1996).
Lander, E. S., et al., "Array of Hope". Nature Genetics Supplement, Perspective, vol. 21, pp. 3-4, (Jan. 1999).

(56) References Cited

OTHER PUBLICATIONS

Latour, P., et al., "Polymorphic Short Tandem Repeats for Diagnosis of the Charot-Marie-Tooth IA Duplication". Clinical Chemistry, vol. 47, pp. 829-837 (2001).
Lau, F. Y., et al., "Provision of phenotype-matched blood units: no need for pre-transfusion antibody screening", Haematologica, vol. 86, No. 7, Jul. 2001, pp. 742-748.
Lee et al. "Quantitation of residual WBCs in filtered blood components by high-throughput, real time kinetic PCR", Blood Components, transfusion, vol. 42, pp. 87-93 (Jan. 2002).
Lee, et al., "Combination of Insulin-like Growth FActor (IGF)-1 and IGF-Binding Protein-1 Promotes Fibroblast-Embedded Collagen Gel Contraction". Endocrinology, vol. 137, pp. 5278-5283 (1996).
Lee, H. J., et al., "Fabricating RNA Microarrays with RNA-DNA Surface Ligation Chemistry". Analytical Chemistry, vol. 77, No. 23, pp. 7832-7837 (Dec. 1, 2005).
Lee, S., et al., "Control of Core-Shell Latex Morphology". Polymer Latexes, ACS Symposium, American Chemical Society, pp. 234-253 (1992).
Lemieux: "high throughput single nucleotide polymorphism genotyping technology" Current Genomics. vol. 1:301-311 (2000).
Lhomme et al. "Abasic DNA structure, reactivity and recognition". Biopolymers. vol. 52 : 65-83 (1999).
Li, A., et al., "Multiplexed analysis of polymorphisms in the HLA gene complex using bead array chips". Tissue Anitigens, vol. 63, pp. 518-528 (2004).
Liang L., et al., "Preparation of Composite-Crosslinked Poly(N-isopropylacrylamide) Gel Layer and Characteristics of Reverse Hydrophilic-Hydrophobic Surface", Journal of Applied Polymer Science, vol. 72, pp. 1-11 (1999).
Liang, L., et al., "Temperature-sensitive membranes prepared by UV photopolymerization of N-isopropylacrylamide on a surface of porous hydrophilic polypropylene membranes", Journal of Membrane Science, vol. 162, pp. 235-246 (1999).
Liebert, M. R., et al., "Dynamics of the holes in human erythrocyte membrane ghosts". J. Biological Chemistry, vol. 257, No. 19, pp. 11660-11666 (1982).
Lin et al. "Raman Studies of Bovine Serum Albumin". Biopolymers 15:203-218 (1976).
Lindahl et al., "Rate of depuriniation of native deoxyribonucleic acid". Biochemistry. vol. 11, No. 19: 3610-1617 (1972).
Lindahl et al., "Rate of chain breakage at apurinic sites in double-stranded deoxyribonclueic acid" Biochemistry, vol. 11, No. 19:3618-3623 (1972).
Lipshutz, R. J., et al., "High Density Synthetic Oligonucleotide Arrays". vol. 21, pp. 20-24 (Jan. 1999).
Liu, et al., "Development of a Carbon Dioxide-Base Microencapsulation Technique for Aqueous and Ethanol-Based Latexes". Langmuir (2002).
Liu, V, et al, "Three-Dimensional Photopatterning of Hydrogels Containing Living Cell". Biomedical Microdevices, vol. 4, No. 4, pp. 257-266 (2002).
Lofas, et al., "Methods for site controlled coupling to carboxymethyldextran surfaces in surface plasmon resonance sensors". Biosensors & Bioelectronics, vol. 10, pp. 813-822 (1995).
Loomans, E., et al., "Assessment of the functional affinity constant of monoclonal antibodies using an improved enzyme-linked immunosorbent assay". Journal of Immunological Methods, vol. 184, pp. 207-217 (1995).
Ye et al., "Fluorescent Microsphere-Based Readout Technology for Multiplexed Human Single Nucleotide Polymorphism Analysis and Bacterial Identification" Human Mutation, Apr. 17, 2001 (4); 305-16).
Lund et al. Assessment of Methods for Covalent Bonding of Nucleic Acids to Magnetic Beads, Bynabeads, and the Characteristics of the Bound Nucleic Acids in Hybridization Reactions, Nucleic Acids REsearch vol. 16, No. 22, 10861-10880 (1988).
Luo et al., "Emulsion Copolymerization of Butyl Acrylate with Cationic Monomer Using Interfacial Redox Initiator System". Journal of Polymer Science, vol. 39, pp. 2696-2709 (2001).

Lvov, Y, et al., "Alernate Assembly of Ordered Multi layers of SiO2 and Other Nanoparticles and Polyions". Langmuir, vol. 13, pp. 6195-6203 (1997).
MacBeath et al., "Printing proteins as microarrays for high-throughput function determination". Science, vol. 289; pp. 1760-1763 (Sep. 8, 2000).
Maldonado-Rodriguez et al., "Hybridization of glass-tethered oligonucleotide probes to . . . ", Molecular Biotechnology, vol. 11, No. 1, pp. 1-12 (1999).
Marras et al., Multiplex detection of single-nucleotide variations using molecular beacons: Genetic Analysis: Biomolecular Engineering 14 (1999) 151-156.
Marsh, S. G. E., et al., The HLA Facts Book, "HLA Typing at the DNA Level", Academic Press, Chapter 6, pp. 37-39 (2000).
Martin, M., et al. "A Method for Using Serum or Plasma as a Source of DNA for HLA Typing". Human Immunology, vol. 33, pp. 108-113 (1992).
Martinell, J. et al., "Three mouse models of human thalassemia", Proc. Natl. Acad. Sci, USA. Aug. 1981, vol. 78, No. 8, pp. 5056-5060 (see especially p. 5057, col. 1, last paragraph, Figure 4, and the legend to Figure 4.
Maskos, U. et al., "Parallel analysis of oligodeoxyribonucleotide (oligonucleotide) interactions. I. Analysis of factors influencing oligonucleotide duplex formation". Nucleic Acids Research, vol. 20, No. 7, pp. 1675-1678 (1992).
Maskos, U., et al., "Oligonucleotide hybridisations on glass supports: a novel linker for oligonucleoptide synthesis and hybridisation properties of oligonucleotides synthesized in situ". Nucleic Acids Research, vol. 20, No. 7, pp. 1679-1684 (1992).
Matthews et al., "Biochemistry: A Short Course". New York: John Wiley & Sons, Inc, p. 25 (1997).
Maxam et al., "A new method for sequencing DNA," Proc. Natl. Acad. Sci. USA. vol. 74, No. 2, pp. 560-564, Feb. 1977.
McCloskey, et al., "Magnetic Cell Separation: Characterization of Magnetophoretic Mobility". Anal. Chem., vol. 75, pp. 6868-6874 (2003).
McCloskey, et al., "Magnetophoretic Mobilities Correlate to Antibody Binidng Capacities". Cytometry, vol. 40, pp. 307-315 (2000).
Mei et al. "Genome-wide Detection of Allelic Imbalance Using Human SNPs and High-Density DNA Arrays". Genome Research. vol. 10, pp. 1126-1137 (2000).
Michael, et al., "Randomly ordered addressable high-density optical ssensor arrays". Anal. Chem, vol. 70, pp. 1242-1248 (1999).
Micheletto et al., "A simple method for the production of a two-dimensional ordered array of small latex particles". Langmuir, vol. 11, pp. 3333-3336 (1995).
Moller, E., et al., "The Use of Magnetic Beads Coated with Soluble HLA Class I or Class II Proteins in Antibody Screening and for Specificity Determination of Donor-Reactive Antibodies", Transplantation, vol. 61, No. 10, pp. 1539-1545 (May 27, 1996).
Moore, et al., "The use of magnetite-doped polymeric microspheres in calibrating cell tracking velocimetry". J. Biochem. Biophys. Methods, vol. 44, pp. 115-130 (2000).
Morag et al. "Immobilized nitro-avidin and nitro-streptavidin as reusable affinity matrices for application in avidin-biotin technology". Analytical Biochemistry. vol. 243: 257-263 (1996).
Mori, et al., Computer program to predict liklihood of finding an HLA-matched donor: Methodology, validation, and application. Biology of Blood and Marrow Transplantation, vol. 2, pp. 134-144 (1996).
Morishima et al., "Microflow system and transportation of DNA molecule by dielectrophoretic force utilizing the conformational transition in the higher order structure of DNA molecule". Proceedings—IEEE Annual International Workshop on Micro Electro Mechanical Systems: An investigation of micro structures, sensors, actuators, machines and robots. Nagoya, Jan. 26-30, 1997.
Muller et al., "Gene and Haplotype Frequencies for the Loci HLA-A, HLB-B, and HLA-DR Based on Over 13,000 German Blood Donors". Human Immunology, 2003, 64: 137-151.
Mullis et al. Specific Synthesis of DNA in Vitro via a Polymerase-Catalyzed Chain Reaction Methods in Enzymology, 1987; vol. 155, pp. 335-350.

(56) References Cited

OTHER PUBLICATIONS

Nagarajan et al., "Identifying Spots in Microarray Images", IEEE Transactions on Nanobioscience, vol. 1, No. 2, pp. 78-84 (Jun. 2002).
Nagayama et al., "Fabrication of two-dimensional colloidal arrays". Phase Transitions, vol. 45, 185-203 (1993).
Nam, J., et a., "Colorimetric Bio-Barcode Amplification Assay for Cytokines". Anal. Chem., vol. 77, pp. 6985-6988 (2005).
Nau et al., "A Command Processor for the Determination of Specificities fro Matrices of Reactions Between Blood Cells and Antisera". Computers and Biomedical Research, vol. 10, pp. 259-269 (1977).
Nazarenko et al. (2002) Multiplexed quantitiative PCR using self-quenched primers labeled with a single fluorophore. Nucleic Acids Research, 30 (9), e37.
Niemeyer et al., "DNA-directed Immobilization: Efficient, Reversible, and Site-Selective Surface Binding of Proteins by means of Covalent Stretavidin Conjugates". Analytical Biochemistry, vol. 268, pp. 54-63 (1999).
Niemeyer et al., "Oligonucleotide-directed self-assembly of proteins: semisynthetic DNA—streptavidin hybrid molecules as connectors for the generation of macroscopic arrays and the construction of supramolecular bioconjugates". Nucleic Acids Research, vol. 22, pp. 5530-5539 (1994).
Nygren, "Molecular Diagnostics of Infectious Diseases" Royal Institute of Technology Department of Biotechnology, Stockholm 2000, pp. 1-68.
Ohlmeyer, M. H. J. et al. "Complex Synthetic Chemical Libraries Indexed with Molecular Tags". Proceedings of the National Academy of Sciences, USA, National Academy of Science, Washington DC. vol. 90, Dec. 1, 1993, pp. 10922-10926.
Okubo, and Yamashita. "Thermodynamics for the preparation of micorn-sized, monodispersed highly monomer-'absorbed' polymer particles utilizing the dynamic swelling method." Colloids and Surfaces, 1999:153-159.
Okubo et al., "Preparation of micron-size monodisperse polymer particles by seeded polymerization utilizing the dynamic monomer swelling method". Colloid and Polymer Science, vol. 269, No. 3, pp. 222-226 (1991).
Olejnik et al., "Photocleavable biotin phosphoramidite for 5'-end-labeling, purification & phosphorylation of oligonucleotides", Nucleic Acids Research 1996, vol. 24, 2:361-366.
Oliver, D., et al, "Use of Single Nucleotide Polymorphisms (SNP) and Real-Time Polymerase Chain Reaction for Bone Marrow Engraftment Analysis". Journal of Molecular Diagnostics, vol. 2, No. 4, pp. 202-208 (Nov. 2000).
Olson et al. "A common langauage for physical mapping of the human genome". Science, vol. 245, pp. 1434-1435 (1989).
Otero, T. F., et al., "Electrochemically initiated acrylic acid/acrylamide copolymerization", J. Electroanal. Chem., vol. 256, pp. 433-439 (1998).
Otero, T. F., et al., "Electroinitiated polymerization of acrylamide in DMG: Attempts at an interfacial model", J. Electroanal. Chem., vol. 304, pp. 153-170 (1991).
Pastinen, et al., "A System for specific, high-throughput genotyping by allele-specific primer extension on microarrays". Genome Res., vol. 10, pp. 1031-1042 (2000).
Peter, C., et al., "Optical DNA-sensor chip for real-time detection of hybridization events". Fresenius J. Anal. Chem, vol. 371, pp. 120-127 (Jun. 2001); Published online Springer-Verlay 2001.
Wilson, M. R., et al., "A New Microsphere-based Immunofluorescence Assay for Antibodies to Membrane-associated Antigens". Journal of Immunological Methods, vol. 107, pp. 231-237 (1988).
Peterson, et al. "Fiber Optic pH probe for physiological use". Anal. Chem. vol. 52, 864-869 (1980).
Peterson, et al., " Fiber Optic Sensors for Biomedical Applications". Science, vol. 13; pp. 123-127 (1984).
Peytavi et al., "Correlation between microarray DNA hybridization efficiency and the position of short capture probe on the target nucleic acid". Biotechniques, vol. 39, No. 1, pp. 89-96 (2005).

Pooga, M., et al., "Cell-Penetrating constructs regulate galanin receptor levels and modify pain transmission in vivo" Nature Biotechnology, vol. 16, pp. 857-861 (1998).
Pope. "Fiber optic chemical microsensors employing optically active silica microspheres". SPIE, vol. 2388; pp. 245-256 (1995).
Prati D. et al., DNA Enzyme Immunoassay of the PCR-Amplified HLA-DQ Alpha Gene for Estimating Residual Leukocytes in Filtered Blood Clincial and Diagnostic Laboratory Immunology, Mar. 1995, p. 182-185.
Pregibon et al, "Magnetically and Biologically Active Bead-Patterned Hydrogels". Langmuir, vol. 22, pp. 5122-5128 (2006).
Preza, "Phase Estimation using rotational diversity for differential interference contrast microscopy". Dissertation presented to the Washington University, Server Institute of Technology, Department of Electrical Engineering; St. Louis, MO (Aug. 1998).
Proudinikov et al., "Chemical methods of DNA and RNA fluorescent labeling". Nucleic Acids Research. vol. 24, No. 22: 4535-4542 (1996).
Proudnikov , D., et al., "Immobilization of DNA in Polyacrimide Gel for the Manufacture of DNA and DNA-Oligonucleotide Microchips", Analytical Biochemistry, vol. 259, pp. 34-41 (1998).
Quon, R., et al., "Measurement of the Deformation and Adhesion of Rough Solids in Contact". J. Phys. Chem., vol. 103, pp. 5320-5327 (1999).
Rabbany et al., "Assessment of hetrogeneity in antibody displacement reactions". Anal Chem, vol. 69, pp. 175-182 (1997).
Radtchecnko et al., "Core-shell structures formed by the solvent-controlled precipitation of luminescent ScTe nanocrystals on latex spheres". Advanced Materials, vol. 13, No. 22, pp. 1684-1687 (2001).
Radtkey et al., "Rapid, high-fidelity analysis of simple sequence repeats on an electronically active DNA microchip". Nucleic Acids Research, vol. 28, No. 7, p. e17 (2000).
Ramsay, G., "Dna Chips: State-of-the-Art". Nature Biotechnology, vol. 16, pp. 40-44 (Jan. 1998).
Reddy et al., "Determination of the Magnetic Susceptibility of Labeled Particles by Video Imaging". Chemical Engineering Science, vol. 51, No. 6, pp. 947-956 (1996).
Reid M.E., et al., "Novel Dombrock blood group genetic variants . . . ", Blood (ASH Annual Meeting Abstract) 2004, 104: Abstract 383.
Relogio, A. et al., "Optimization of oligonucleotide-based DNA microarrays", Nucl. Acids Res., vol. 30, e51, pp. 1-10 (2002).
Richardson et al., "The use of coated paramagnetic particles as a physical label in a magneto-immunoassay". Biosensors & Bioelectronics, vol. 16, pp. 989-993 (2001).
Richardson, et al., "A novel measuring system for the determination of paramagnetic particle lables for use in magneto-immunoassays". Biosensors & Bioelectronics, vol. 16, pp. 1127-1132 (2001).
Richetti et al., "Two-dimensional aggregations and crystallization of a colloidal suspension of latex spjeres", J. Physique Letter. vol. 45, pp. L-1137 to L-1143 (1984).
Righetti, P. G., et al., "Electrophoresis gel media: the state of the art", J. Chromatogr B., Biomed Sci Appl, vol. 699, No. 1-2, pp. 63-75 (Oct. 10, 1997).
Roberts et al. "Patterned magnetic bar array for high-thoughput DNA detection" IEEE Transaction on Magnetics. vol. 40, No. 4: 3006-3008 (2004).
Rubina et al, "Hydrogel drop microchips with immobilized DNA: properties and methods for large-scale production". Analytical Biochemistry, vol. 325, pp. 92-106 (2004).
Rudzinski, et al., "pH-sensitive acrylic-based copolymeric hydrogels for the controlled release of a pesticide and a micronutrient". Journal of Applied Polymer Science, vol. 87, pp. 394-403 (2003).
Sacchetti, et al. "Efficiency of Two Different Nine-Loci Short Tandem Repeat Systems for DNA Typing Purposes". Clinical Chemistry, vol. 45, No. 2, pp. 178-183 (1999).
Saito, K., et al., "Detection of Human Serum Tumor Necrosis Factor-alpha in Healthy Donors, Using a Highly Sensitive Immuno-PCR Assay". Clinical Chemistry, vol. 45, No. 5, pp. 665-669 (1999).
Sambrook et al,, "Precipitation with Ethanol or Isopropanol", Concentrating Nucleic Aicds, Molecular Cloning vol. 3, pp. E3-E4 and E.10-E.15 (1989).

(56) References Cited

OTHER PUBLICATIONS

Sano, T, et al., "Immuno-PCR: Very Senisitive Antigen Detection by Means of Specific Antibody-DNA Conjugates". Science, vol. 258, pp. 120-122 (Oct. 2, 1992).
Santa Lucia, J. Jr., "A unified view of polymer, dumbbell, and oligonucleotide DNA nearest-neighbor thermodynamics". PNAS USA, vol. 95, pp. 1460-1465 (1998).
Schaid et al., "Score Tests for Association between traits and Haplotypes when linkage Phase is Ambiguous", American Journal of Genetics. vol. 70, pp. 425-434 (2002).
Schena et al., "Quantitative Monitoring of Gene Expression Patterns with a Complementary DA Microarray". Science, vol. 270, pp. 467-470 (1995).
Schouten, Jan P., et al., "Relative Quantification of 40 Nucleic Acid Sequences by Multiplex Ligation-Dependent Probe Amplification". Nucleic Acids Research, vol. 30, No. 12, e57 (Jun. 15, 2002).
Schreiber, G. B., et al., "Increasing Blood Availability by changing Donation Patterns". Transfusion, vol. 43, pp. 591-597 (2003).
Schreuder et al., "The HLA Dictionary 1999: A Summary of HLA-A, B, C, DRB1/3/4/5, DOB1 alleles and their association with serologically defined HLA-A, B, C, DR and DQ antigens", Tissue Antigens 54 : 409-437 (1999).
Schumaker, et al., "Mutation Detection by solid phase primer extension", Human Mutation 7:346-354 (1996).
Wilson et al., "A generalized method for magnetite nanoparticle steric stabilization utilizing block copolymers containing carboxylic acids". European Cells and Materials, vol. 2, Suppl 2, pp. 202-209 (2002).
Schuster et al. "Allele-specific and asymetric polymerase chain reacton amplification in combination: a one step polymerase chain protocol for rapid diagnosis of familial defective apolipoprotein B-100", Anal Biochem. Jul. 1992; 204 (1):22-5).
Scillian, James J., et al., "Early Detection of Antibodies Against rDNA-Produced HIV Proteins with a Flow Cytometric Assay". Clinical Chemistry, vol. 40, No. 3, pp. 420-425 (1994).
Scott et al., "Properties of Fluorophores on solid phase resins; Implications for screening, encoding and reaction monitoring". Bioorganic & Medicinal Chemistry Letter, vol. 7, No. 12, pp. 1567-1572 (1997).
S. Dubiley et al., "Polymorphism Analysis and Gene Detection by minsequencing on an array of gel immobilized primers." Nucleic Acids Research, 1999;i-vi. vol. 27, No. 16.
S. Ebel et al. "Very Stable Mismatch Duplexes: Structural and Thermodynamic Studies on G-A Mismatches in DNA" Biochemistry 31:12083-86 (1992).
Seeman, P., et al., "Structure of Membrane Holes in Osmotic and Saponin Hemolysis"; The Journal of Cell Biology, vol. 56; pp. 519-527 (1973).
Sehgal et al. "A method for the high effieiency of water-soluble carbodiimide-mediated amidation". Analytical Biochemistry. vol. 218:87-91 (1994).
Seltsam, et al., Systematic analysis of the ABO gene diversity within exons 6 and 7 by PCR screening reveals new ABO alleles, Transfusion, vol. 43, pp. 428-439 (2003).
Sennerfors, T., et al., "Adsorption of Polyelectrolyte-Nanoparticle Systems on Silica: Influence of Ionic Strength". Journal of Colloid and Interface Science, vol. 254, pp. 222-226 (2002).
Serizawa, T., et al., "Electrostatic Adsorption of Polystyrene Nanospheres onto the Surface of an Ultrathin Polymer Film prepared by Using an Alternate Adsorption Technique". Langmuir, vol. 14, pp. 4088-4094 (1998).
Sethu, P; "Microfluidic diffusive filter for apheresis (leukopheresis)"; Lab Chip, vol. 6, No. 1, pp. 83-89 (Jan. 2006); Published electronically Nov. 11, 2005.
Seul et al., "Domain Shapes and Patterns: The Phenomenology of Modulated Phases". Science, vol. 267:476-483 (1995).
Seul et al., "Scale transformation of magnetic bubble arrays: coupling of topological disorder and polydispersity". Science, vol. 262: 558-560 (1993).
Sgaramella, V., et al., "Total Synthesis of the Structural Gene for an Alanine Transfer RNA from Yeast. Enzymic Joining of the Chemically Synthesized Polydeoxynucleotides to form the DNA Duplex Representing Nucleotide Sequence 1 to 20". J. Mol. Biology, vol. 72, pp. 427-444 (1972).
Sham , P. et al., "Haplotype Association of Discrete and Continuous Traits Using Mixture of Regression Models", Behavior Genetics, Mar. 2004, 34(2), pp. 207-214.
Shevkoplyas, S., et al., "Biomimetic autoseparation of leukocytes from whole blood in a microfluidic device"; American Chemical Society; vol. 77, No. 3, pp. 933-937 (Feb. 1, 2005).
Shon. "Application Note—New Best Practices for Biosample Management: Moving Beyond Freezers". American Biotechnology Laboratory, vol. 23, No. 2, pp. 10-13 (2005).
Shoyer, Terrie W., et al., "A Rapid Flow Cytometry Assay for HLA Antibody Detection Using a Pooled Cell Panel Convering 14 Serological Crossreacting Groups". Transplantation, vol. 59, No. 4, pp. 626-630 (1995).
Siegel, D., "Phage display-based molecular methods in immunohematology". Transfusion, vol. 47, pp. 89S-94S (Jul. 2007 Supplement).
Simon, R. "Application of optimization methods to the hematological support of patients with disseminated malignacies", Mathematical Biosciences, vol. 25, 1975, pp. 125-138.
Skalnik et al., "A Rapid Method for Characterizing transgenic Mice", S. Biotechniques 8:34 (1990).
Skolnick et al. "Simultaneous analysis of multiple polymorphic loci using amplified sequence polymorphisms (ASPS)". Genomics, vol. 2, pp. 273-279 (1988).
Smay, J., et al., "Colloidal Inks for Directed Assembly of 3-D Peridoic Structures". Langmuir, vol. 18, pp. 5429-5437 (2002).
Smith, J. W., et al., "RED: A Red-Cell Antibody Identification Expert Module". Journal of Medical Systems, vol. 9, No. 3, pp. 121-138 (1985).
Southern E. M., "DNA Fingerprinting by hybridisation to oligonucleotide arrays". Electrophoresis, vol. 16, No. 9, pp. 1539-1542 (1995).
Southern, E. M., et al., "Analyzing and comparing nucleic acid sequences by hybridization to arrays of oligonucleotides: evaluation using experimental models". vol. 13, No. 4, pp. 1008-1017 (Aug. 1992).
St. Louis, M, et al., "The Dombrock blood group system: A Review", Transfusion 43: 1126-1132 (2003).
Steemers, F.J. (2000) Screening unlabeled DNA targets with randomly ordered fiber-optic gene arrays. Nat. Biotechnol., 18, 91-94.
Stemmer, C., et al., "Use of Magnetic Beads for Plasma Cell-free DNA Extraction: Toward Automation of Plasma DNA Analysis for Molecular Diagnostics". Clinical Chemistry, vol. 49, No. 11, pp. 1953-1955 (2003).
Stevens, P. W., et al. "Imaging and Analysis of Immobilized Particle Arrays". Analytical Chemistry. vol. 75, pp. 1147-1154 (2003).
Storry et al, "Genetic Basis of blood group diversity". British Journal of Haematology, vol. 126, pp. 759-771 (2004).
Strobel E., et al., "The molecular basis of Rhesus antigen E", Transfusion 44:407-409 (2004).
Sukhishvilli, S.A. et al. "Adsorption of human serum albumin: Dependence on molecular architecture of the oppositely charged surface" J. Chem. Phys. 110, 10153-10161 (1999).
Sun et al., "Continuous, Flow-Through Immunomagnetic Cell Sorting in a Quadrupole Field". Cytometry, vol. 33, pp. 469-475 (1998).
Suzawa et al., "Adsorption of Plasma Proteins onto Polymer Latices". Advances in Colloid and Interface Science, vol. 35, pp. 139-172 (1991).
Svitel, et al., "Combined Affinity and Rate Constant Distributions of Ligand Populations from Experimental Surface Binding Kinetics and Equilibria". Biophysical Journal, vol. 84, pp. 4062-4077 (Jun. 2003).
Syvanen, "From Gels to Chips: Minisequencing Primer Extensions for Analysis of Pont Mutations and Single Nucleotide Polymorphisms", Human Mutation 13:1-10 (1999).

(56) References Cited

OTHER PUBLICATIONS

Syvanen, A., et al., "Identification of Individuals by Analysis of Biallelic DNA Markers, Using PCR and Solid-Phase Minisequencing". Am. J. Hum. Genet, vol. 52, pp. 46-59 (1993).
Syvannen, A. "Toward genone-wide SNP genotyping". Nature Genetics Supplement. vol. 37: s5-s10 (2005).
Sze. MIS Diode and Charge-Coupled Device. The Physics of Semiconductors, Chapter 7, pp. 362-430 (2nd Edition) (1981).
Takeda et al. "Conformational Change of Bovine Serum Albumin by Heat Treatment", J. Protein Chemistry 8:653-659, No. 5 (1989).
Tanaka, T., et al "Mechanical instability of gels at the phase transition", Nature, vol. 325, pp. 796-798 (1987).
Taniguchi et al. "Adsorption/desorption behavior and covalent grafting of an antibody onto cationic amino-functionalized poly(styrene-N-isoprapylacrylamide) core-shell latex particles". Colloids and Surfaces B: Biointerfaces. vol. 29: 53-65 (2003).
Tarnok et al., "Cytometric Bead Array to Measure Six Cytokines in Twenty-Five Microliters of Serum," Clinical Chemistry, (2003), vol. 49, No. 6, pp. 1000-1002.
Taylor et al., "Linked oligodeoxynucleotides show binding cooperativity and can selectively impair replication of deleted mitochondrial DNA templates", Nucleic Acids Research. vol. 29, No. 16, pp. 3404-3412 (2001).
Tobitani et al. "Heat-induced gelation of globular proteins. 1. Model for the effects of time and temperature onthe gelation time of BSA gels." Macromolecules. vol. 30:4845-4854 (1997).
Tokumasu F. et al., Development and application of quantum dots for immunocytochemistry of human erythrocytes, J. Microscopy, 2003, pp. 256-261, vol. 211, pt. 3.
Tonisson et al., "Arrayed primer extension on the DNA chip; Method and applications", Microarray Biochip Technology, Biotechniques Books, 247-262 (2000).
Tsuchihashi, Z. et al. "Progress in high throughput SNP genotyping methods", The Pharmacogenomics Journal 2:103-110 (Apr. 2002).
Trau et al., "Field-induced layering of colloidal crystal", Science, vol. 272; pp. 706-709 (1996).
Trang D.T.X. et al. "One step concentration of malarial parasite-infected red blood cells and removal of contaminating white blood cells", Malaria Journal (2004) pp. 1-7 from http://www.malariajournal.com/content/3/1/7.
Trau et al., "Nanoencapsulated microcrystalline particles for superamplified biochemical assays". Anal. Chem, vol. 74, No. 21, pp. 5480-5486. Web Release Date: Sep. 25, 2002.
Turcanu et al, "Cell Identification and isolation on the basis of cytokine secretion: A novel tool for investigating immune responses". Nature Medicine, vol. 7, No. 3, pp. 373-376 (Mar. 2001).
Tyagi et al., Molecular Beacons: Probes that Flouresce upon Hybridization, Nature Biotechnology vol. 14, pp. 303-308 (1996).
Vainrub, A., et al., "Sensitive quantitative nucleic acid detection using oligonucleotide microarrays". Journal of the American Chemical Society, vol. 125, No. 26, pp. 7798-7799, (Jun. 2003).
Van Kempen, et al., "Mean and Variance of Ratio Estimators Used in Fluorescence Ratio Imaging". Cytometry. vol. 39, pp. 300-305 (2000).
Van Zoelen, "Receptor-ligan interaction: a new method for determing binding parameters without a priori assumptions on non-specific binding". Biochem J., vol. 262, pp. 549-556 (1989).
Vasiliskov, A. V., et al., "Fabrication of Microarray of Gel-Immobilized Compounds on a Chip by Copolymerization". BioTechniques, vol. 27, pp. 592-606 (Sep. 1999).
Vaynberg et al. "Structure and extent of absorbed gelatin on acrylic latex and polystyrene collodial particles". Journal of Colloid and Interface Science. vol. 205:131-140 (1998).
Vet, J.A.M. (1999) Multiplex detection of four pathogenic retroviruses using molecular beacon. Proc. Natl. Acad. Sci. USA, 96, 6394-6399.
Vilain. "CYPs, SNPs, and Molecular Diagnosis in the Postgenomic Era". Clinical Chemistry, vol. 44, pp. 2403-2404 (1998).
Wahl et al., "Efficient transfer of large DNA fragments from agarose gels to diazobenzyloxymethyl-paper and rapid hybridization by using dextran sulfate". Proc. Natl. Acad. Sci. USA. vol. 76, No. 8: 3683-3687 (1979).
Wang, D., et al, "Large-Scale Identification, Mapping, and Genotyping of Single-Nucleotide Polymorphisms in the Human Genome". Science, vol. 280, No. 5366, pp. 1077-1082 (May 15, 1998).
Warren, J. A., "Selected Spacings During Directional Solidification of a Binary Alloy", Spatio-Temporal Patterns, Ed. P. E., Cladis and P. Palffy-Muhoray, SFI Studies in the Science of Complexity, Addison-Wesley, pp. 91-105 (1995).
Weinfeld et al., "Selective hydrolysis by exo- and endonucleases of phosphodiester bonds adjacent to an apurinic site". Nucleic Acids Research, vol. 17, No. 10: 3735-3744 (1989).
Weissenbach et al. "A Second generation linkage map of the human genome". Nature, vol. 359, pp. 794-801 (1992).
Wen, et al., "Planar Magnetic Colloidal Crystals". Physical Review Letters, vol. 85, No. 25, pp. 5464-5467 (2000).
Wiedmann, M., et al., Ligase Chain Reaction (LCR)—Overview and Applications, PCR Methods and Applications, Genome Research, vol. 3, pp. s51-s64 (1994).
Yeang et. al. Molecular classification of multiple tumor types. Bioinformatics vol. 17 Suppl. 1, pp. s316-s322 (2001).
J.F. Chapman et al., "Working Party of the BCSH: Guidelines for compatibility procedures in blood transfusion laboratories", Transfusion Medicine, vol. 14, pp. 59-73 (2004).
Yamashita et al., "Thermodynamics for the preparation of micron-sized, monodispersed highly monomer absorbed polymer particles utilizing the dynamic selling method". Colloids and Surfaces, vol. 153, pp. 153-159 (1999).
Yao et al., "Molecular-beacon-based array for sensitive Dna analysis". Analytical Biochemistry, vol. 331, pp. 216-223 (2004).
Fukuda et al., "Noncontact manipulation of DNA molecule 1. Transportation of DNA molecule by dielectric force". Nippon Kikai Gakkai Ronbunshu, vol. 62: 2765-2772 (1996).
Friedli, Interaction of SWP with Bovine Serum Albumin (BSA) and Soluble Wheat Protein (SWP) (7 pages) downloaded http://www.friedli.com/research/PhD/chapter5a.html.
Hermanson, Greg T., "Zero Length Cross-Linkers"; Bioconjugate Techniques; Academic Press, pp. 170-176 (1996).
Hermanson, Greg T., "Bioconjugate Techniques", Bioconjugate Techniques; Academic Press, San Diego, 430-33, (1996).
MacBeath et al., "Printing proteins as microarrays for high-throughput function determination," Science vol. 289: 1760-1763 (2000).
Tobitani et al. "Heat-induced gelation of globular proteins 2. Effect of environmental factors on single-component and mixed-protein gels," Macromolecules; vol. 30: 4855-4862 (1997).
Wittemann et al., "Interaction of Proteins with Spherical Polyelectrolyte Brushes" (Polyer Institute, University of Karisruhe, Karisruhe, Germany) Poster Oct. 2001.

\* cited by examiner

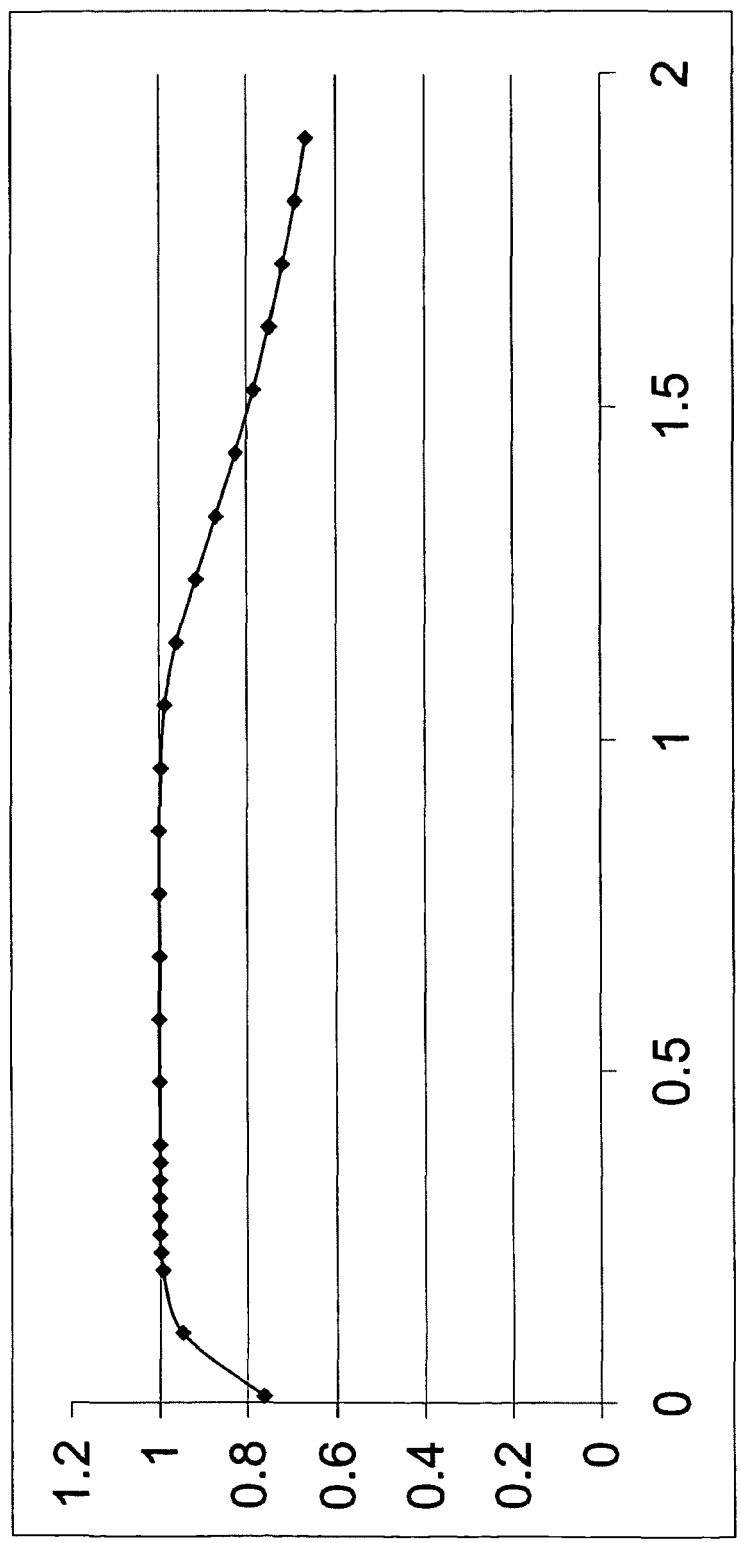
Fig. 1B: Exemplary Empirical Threshold Determination for One Probe

Assignment Adjustment

Assignment Tolerance

HLA-A: 6    HLA-B: 8    HLA-DR: 5

Probe List:

| Probe Name | Required | High Confidence | Low Confidence | Not Used |
|---|---|---|---|---|
| HA114 | | X | | |
| HA114AT | | | | X |
| HA115 | | X | | |
| HA116 | | X | | |
| HA119 | | | X | |
| HA120 | | X | | |
| HA121 | | | X | |
| HA122 | | X | | |
| HA122AT | | | | X |
| HA122B | | | | X |
| HA123 | | X | | |

Scroll Bar

Fig. 1C: System Settings

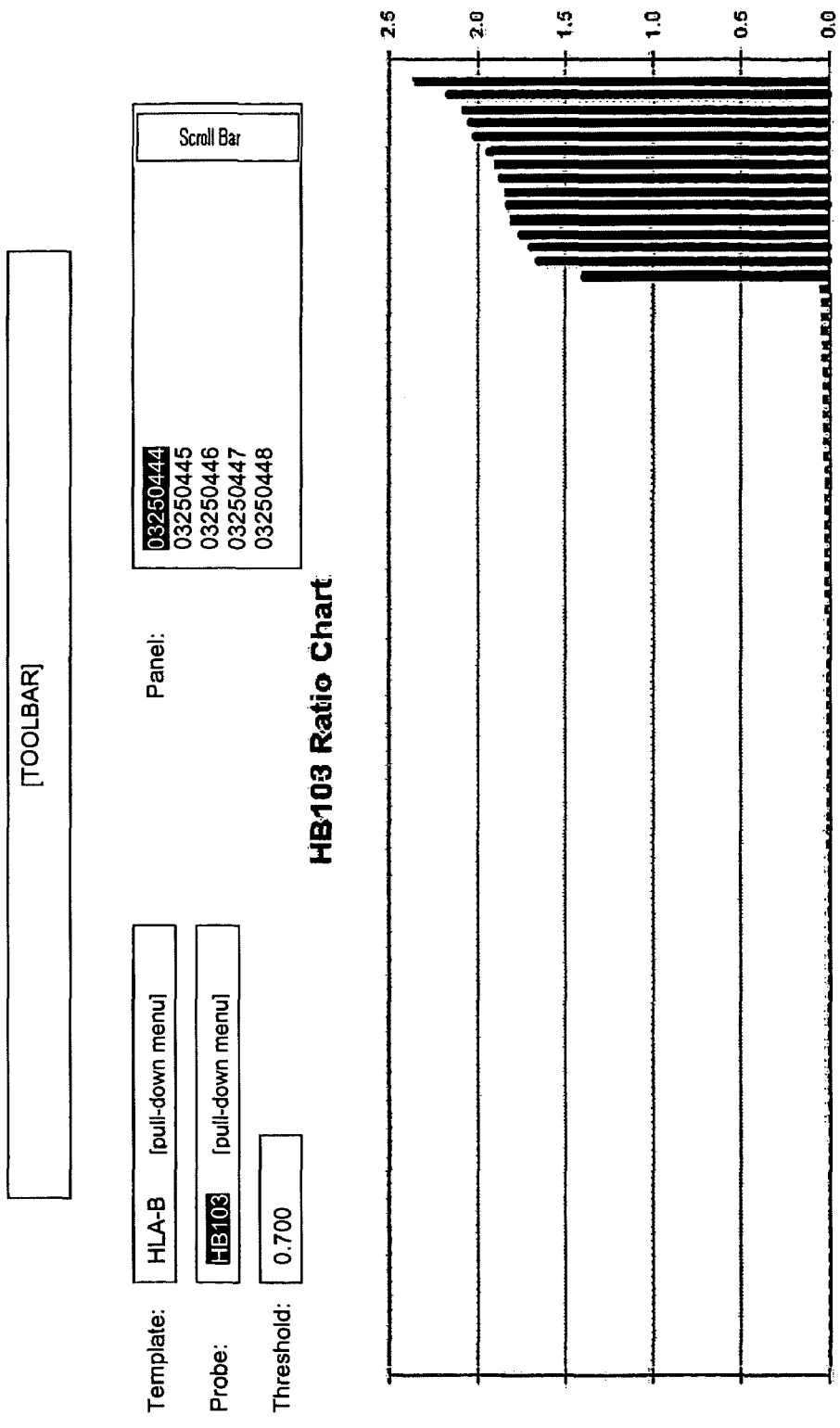
FIG. 2A HB103 Probe Ratio Profile

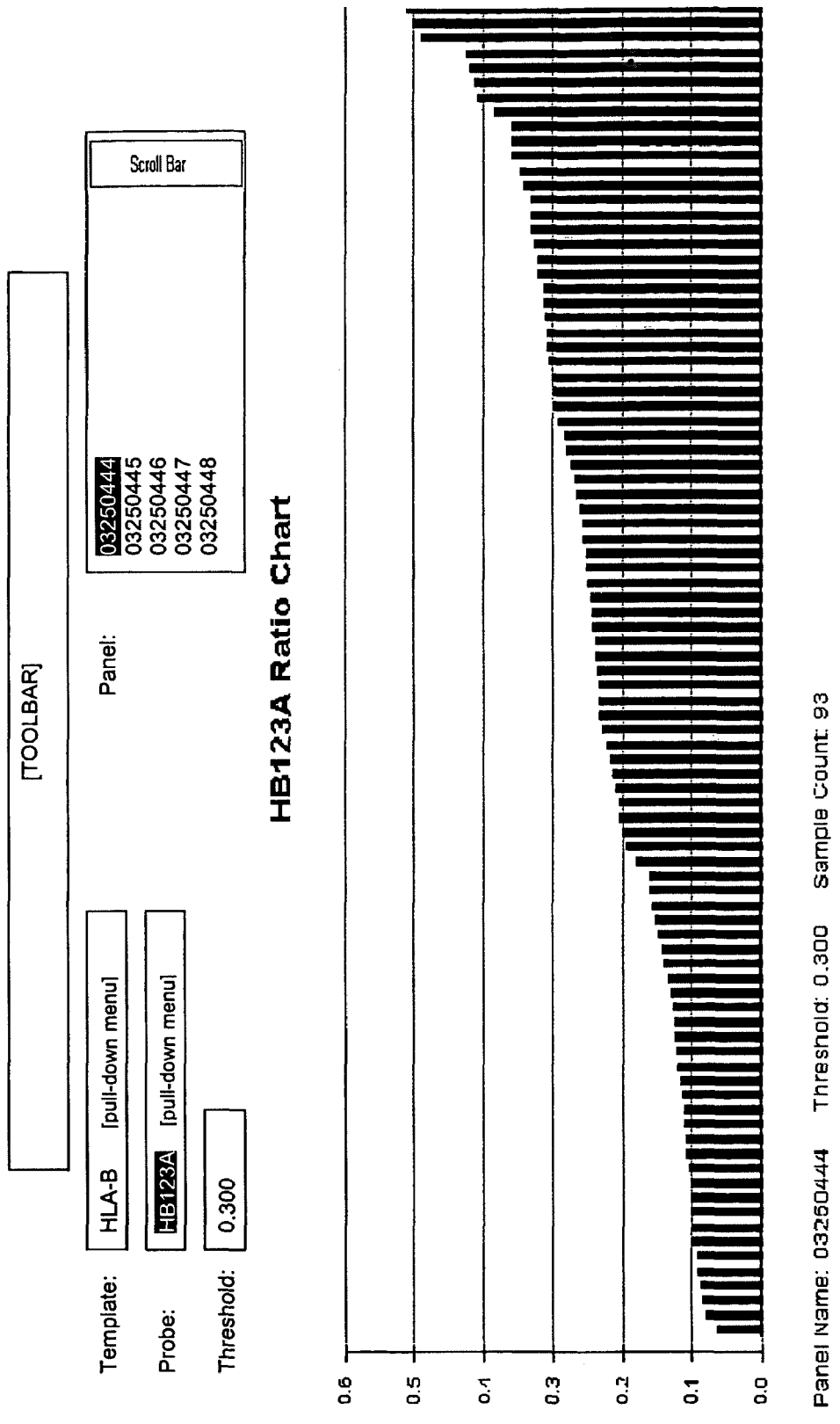
FIG. 2B HB123A Probe Ratio Profile

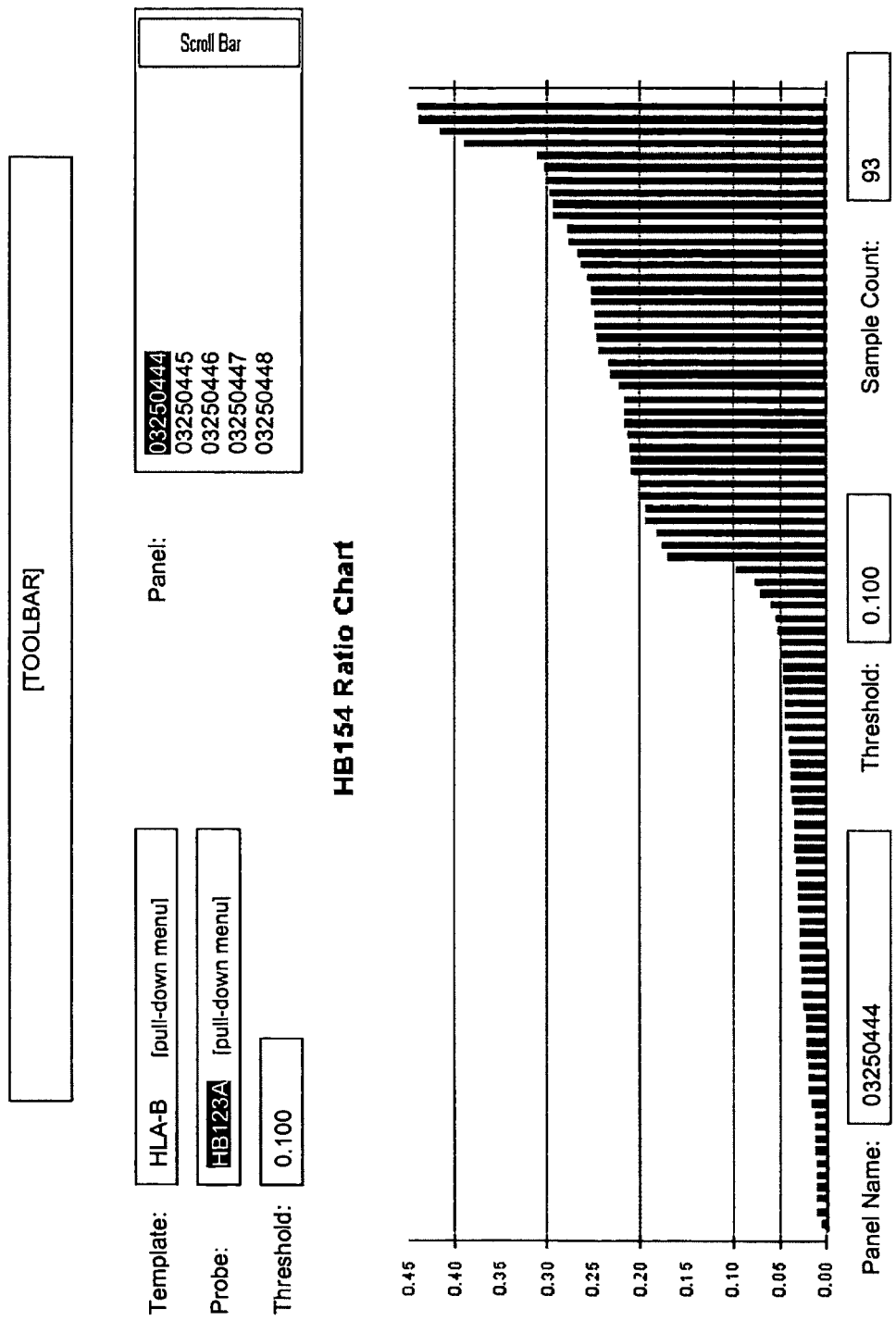
FIG. 2C HB154 Probe Ratio Profile

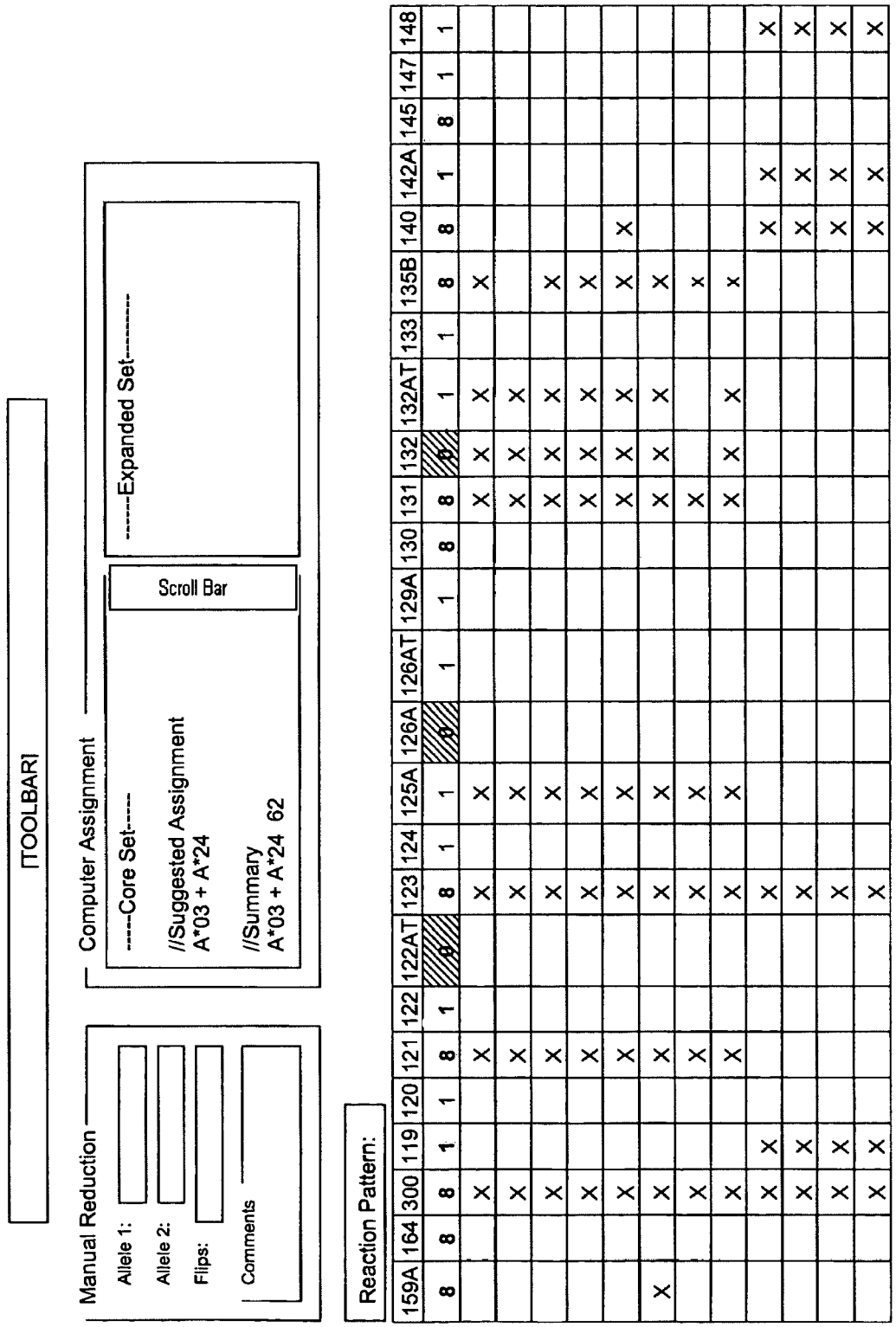
Fig. 3: Allele assignment

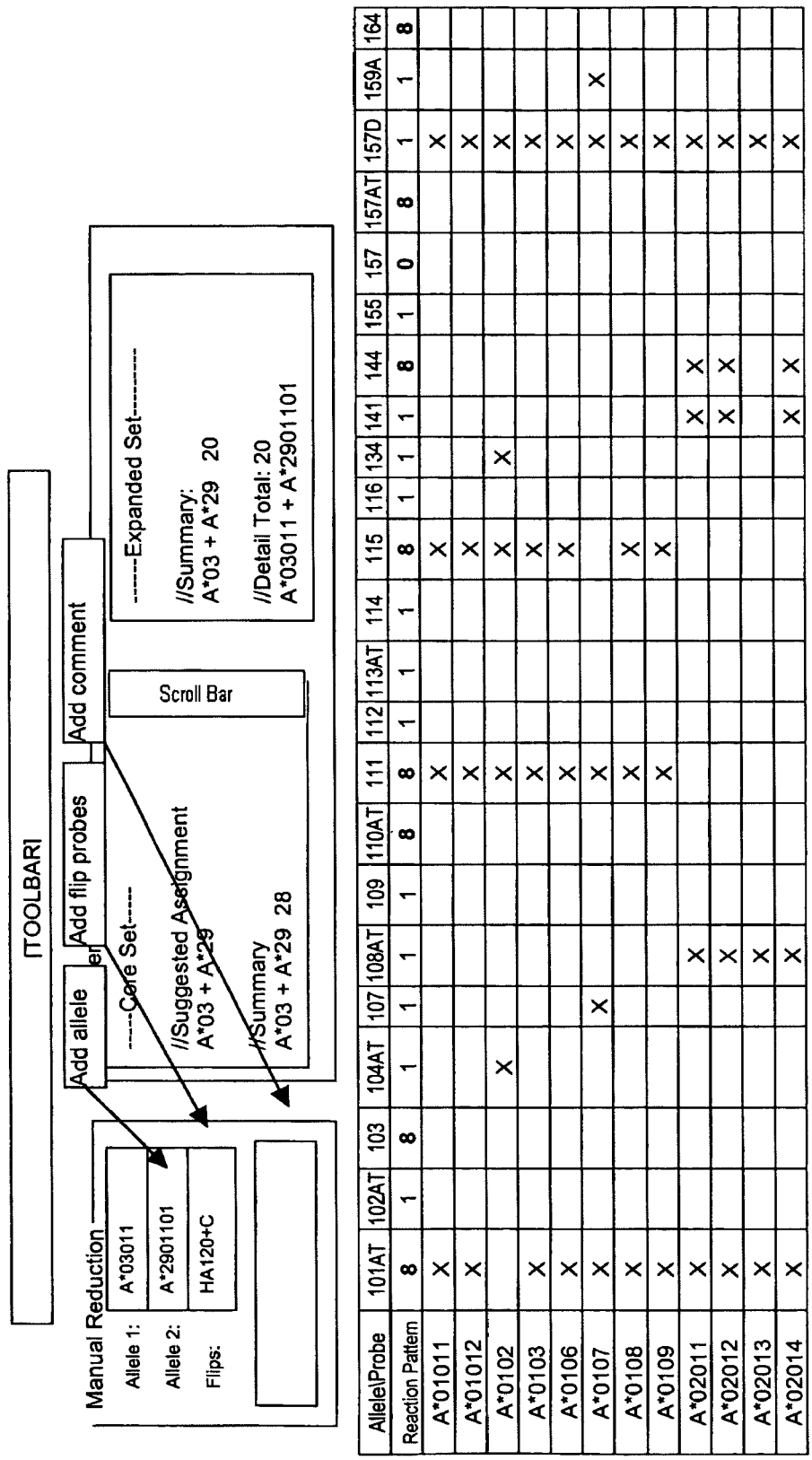
Fig. 4: Allele assignment with manual redaction

Search Criteria  
Sample Name: [MENU]

| HLA-A | | | | | | | | | |
|---|---|---|---|---|---|---|---|---|---|
| Panel Name | Sample Name | Position | Allele1 | Allele2 | # Group | # Allele | Flips | Flip Probe | Warning Message | Comments |
| 3250443 | D020157 | A2 | A*24(02101) | A*26(01) | 1 | 45 | 0 | | | |
| 3250443 | D020169 | B2 | A*02011 | | 0 | 0 | 0 | (HA163+D)(Manual) | | OK |
| 3250443 | D020181 | C2 | A*01(011) | A*29(01101) | 1 | 25 | 0 | | | |
| 3250443 | D020193 | D2 | A*3001 | | 2 | 2 | 0 | | | okay |
| 3250443 | D020205 | E2 | A*26(01) | A*30(01) | 1 | 4 | 0 | | | |
| 3250443 | D020217 | F2 | A*01(011) | A*03(011) | 1 | 31 | 0 | | | |
| 3250443 | D020229 | G2 | A*01(011) | A*29(01101) | 1 | 25 | 0 | | | |
| 3250443 | D020241 | H2 | A*01(011) | A*32(01) | 1 | 10 | 0 | | | |
| 3250443 | D020158 | A3 | A*0302 | A*58(011) | 1 | 2 | 0 | | | |
| 3250443 | D020170 | B3 | A*01(011) | A*02(011) | 1 | 91 | 0 | | | okay |
| 3250443 | D020182 | C3 | A*02(02) | A*02(10) | 2 | 71 | 1 | HA157AT+C | | |
| 3250443 | D020194 | D3 | A*03(011) | A*24(02101) | 1 | 62 | 0 | | | |
| 3250443 | D020206 | E3 | A*11(011) | A*3001 | 1 | 7 | 0 | | | |
| 3250443 | D020218 | F3 | A*01(011) | A*03(011) | 1 | 31 | 0 | | | |
| 3250443 | D020230 | G3 | A*01(011) | A*02(02) | 1 | 8 | 0 | | | |
| 3250443 | D020242 | H3 | A*01(011) | A*24(02101) | 1 | 61 | 0 | | | |
| 3250443 | D020158 | A4 | A*02011 | A*58011 | 0 | 0 | 0 | (HA129A-C)(Manual) | | could be OK |
| 3250443 | D020171 | B4 | A*03(011) | A*3001 | 1 | 7 | 0 | | | |
| 3250443 | D020183 | C4 | A*02(011) | A*24(02101) | 1 | 209 | 0 | | | |
| 3250443 | D020195 | D4 | A*01(011) | | 3 | 26 | 0 | | | expanded set, OK |
| 3250443 | D020207 | E4 | A*01(011) | A*02(011) | 1 | 91 | 0 | | | |
| 3250443 | D020219 | F4 | A*01(011) | A*03(011) | 1 | 31 | 0 | | | |
| 3250443 | D020231 | G4 | A*02(011) | A*26(01) | 1 | 71 | 0 | | | |
| 3250443 | D020243 | H4 | A*0302 | A*6901 | 1 | 1 | 0 | | | |
| 3250443 | D020160 | A5 | A*01(011) | A*68(012) | 1 | 32 | 0 | | | |
| 3250443 | D020172 | B5 | A*0205 | A*2402101 | 0 | 0 | 0 | (HA157AT+C)(Manual) | | okay |

Fig. 7

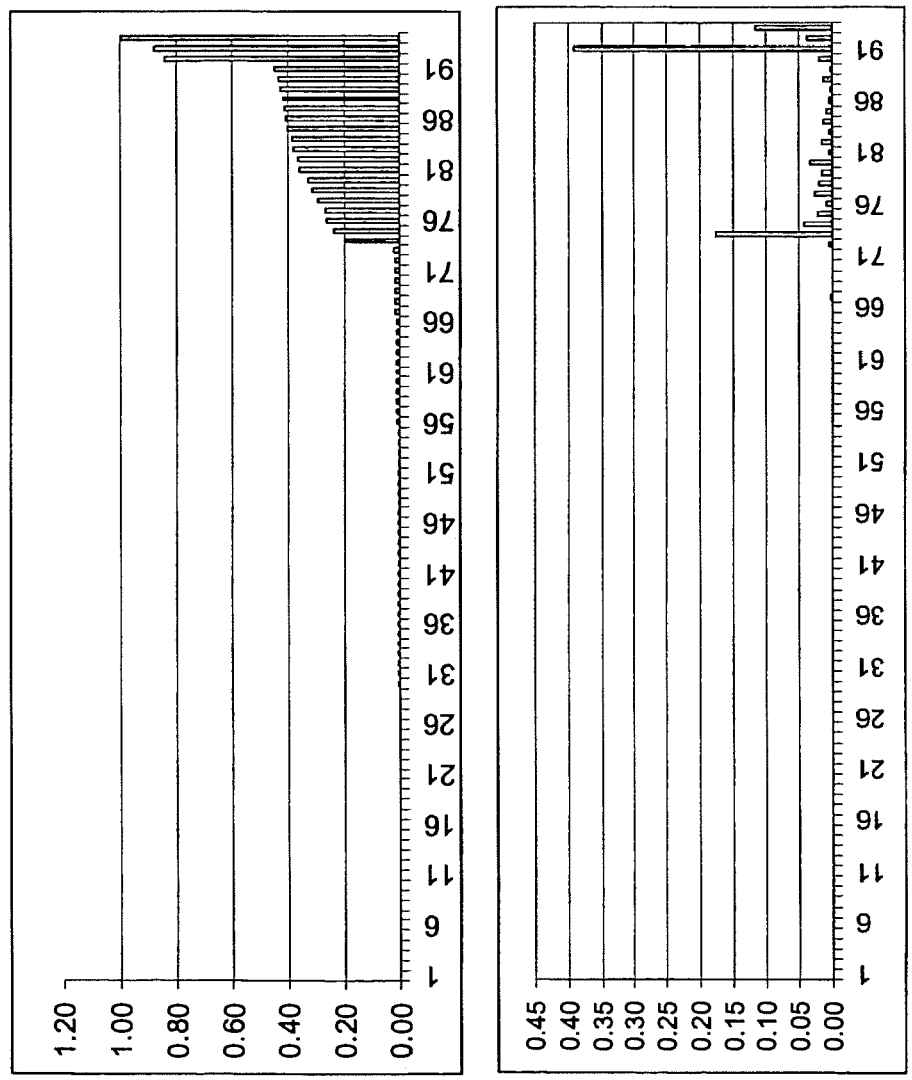
Fig. 8A (upper panel); Fig. 8B (lower panel)

AUTOMATED ANALYSIS OF MULTIPLEXED PROBE-TARGET INTERACTION PATTERNS: PATTERN MATCHING AND ALLELE IDENTIFICATION

RELATED APPLICATIONS

This application is a continuation of U.S. application Ser. No. 12/961,086, filed Dec. 6, 2010, now abandoned which is a continuation of U.S. application Ser. No. 10/909,638 (now U.S. Pat. No. 7,848,889), filed on Aug. 2, 2004, the content of which is incorporated herein by reference in its entirety.

Complex Interaction Patterns as Diagnostic Markers—Parellel assay formats, permitting the concurrent ("multiplexed") analysis of multiple genetic loci in a single reaction, arc well suited to the determination of specific target configurations ("alleles") encountered in a given sample and to the monitoring of quantitative markers such as expression levels of designated genes or levels of circulating protein biomarkers which manifest themselves in receptor-ligand interaction patterns. In what follows, reference to probe-target interactions is meant to refer to this more general situation. By interrogating the target(s) with a selected set of oligonucleotide probes (see, e.g., U.S. Pat. No. 5,837,832, entitled "Arrays of nucleic acid probes on biological chips") and analyzing the patterns of specific interactions of one or more target sequences with that probe set, alleles and allele combinations can be rapidly identified.

This diagnostic capability likely will play an increasingly important role in the study of complex diseases such as arthritis, diabetes and cancer, including the assessment of predisposition to develop a disease having complex inheritance, and requiring the interpretation of an entire set of molecular markers. However, the analysis of the results—in the form of a pattern of intensity readings produced in a multiplexed assay reflecting the strength of interaction of one or more target(s) with the selected set of probes—faces the formidable challenge of interpreting the interaction pattern by mapping it to valid allele combinations or by assessing predisposition or risk, while also ascertaining the reliability and "uniqueness" of the assignment.

A Model: HLA Molecular Typing—The analysis of polymorphisms in the Human Leukocyte Antigen (HLA) gene complex provides a model of the complexity involved in analyzing disease association, thereby serving to delineate the requirements to be addressed by rapid and reliable automated analysis. The HLA complex comprises multiple highly polymorphic loci which encode variable antigens mediating an immune response to "foreign" bone marrow or tissue. At present, 282 HLA-A, 540 HLA-B and 136 HLA-C class I alleles, and 418 HLA-DRB, 24 HLA-DQA1 and 53 HLA-DQB1 class II alleles have been identified. Many known allele sequences appear in public databases, for example, the IMGT/HLA database, www.ebi.ac.uk/imgt/hla/intro.html) for human leukocyte antigens.

Parallel ("multiplexed") hybridization assays of various formats have been widely used for HLA molecular typing which requires a unique combination of throughput and reliability in identifying alleles or groups of alleles associated with specific class I and class II antigens. In the context of HLA molecular typing, standard assay methodologies of the art invoke a "reverse dot blot" format. In accordance with this format, probes, placed, in a set of well-separated bands, on a narrow strip of nylon membrane or other substrate material, are exposed to a solution of target(s) under conditions permitting capture of the target(s) to produce, in a subsequent decoration step, colorimetric signals. Other methods of the art include the use of probes displayed on encoded microparticles which are suspended in a target solution and analyzed by flow cytometry (see "Products" http://www.onelambda.com). A recent method provides an integrated assay environment by using planar arrays of encoded microparticles arranged on silicon chips (see, e.g., allowed application Ser. No. 09/690,040, assigned to BioArray Solutions, Ltd.).

The design of parallel assay formats for the analysis of polymorphic loci such as the HLA complex, notably the selection of sets of primer pairs and probes, has been described in the prior art as well as in several co-pending applications (see, e.g., Concurrent Optimization in Selection of Primer and Capture Probe Sets for Nucleic Acid Analysis," filed Jul. 15, 2004 and assigned to BioArray Solutions, Ltd.).

Sequence Complementarity and Binary Representation—The interpretation of probe-target interaction patterns involves the task of matching a binary string ("reaction pattern") derived from an experimental signal intensity pattern to one (or more) allele combinations or establishing the validity of new alleles.

Each allele will have subsequences that are perfectly complementary, and others that are not complementary to probes in a probe set constructed to interrogate the target. This configuration is represented in the art by a binary code which provides the basis for allele assignments. That is, by assigning to each perfectly matched probe a score "+" (herein denoted by "8"), and to each mis-matched probe a score of "−" (herein denoted by "1"), a binary string is constructed to represent the pattern of interaction of the chosen probe set with a specific combination of alleles encountered. The dictionary showing the correspondence between alleles and binary strings is known in the art as the "hit table".

The reaction pattern—produced by the selected set of probes—may correspond to more than a single allele combination, and the degree of ambiguity ("degeneracy") determines the precision ("resolution") attainable in identifying allele combinations. In general, the degree of resolution can be increased by adding probes to the set.

Assay signal intensities reflect the strength of probe-target interactions. An ideal probe produces an assay signal of high intensity when perfectly complementary ("matched") to its target subsequence in a given sample and otherwise produces an assay signal intensity of low intensity. That is, the signal intensity distribution of such a probe over a large sample set, ideally would display two distinct peaks, suggesting a segmentation of signal intensities into subpopulations reflecting "matched" or "mismatched" probe and target sequence configurations.

However, in practice, the interaction of one or more polymorphic target with a multiplicity of probes can produce a wide range of assay signal intensities. For example, otherwise positive assay signal intensities may be reduced, or otherwise negative assay signal intensities may be enhanced, thereby "smearing out" the individual distributions of intensities. For example, probe-target hybridization is weakened when a probe encounters in a target subsequence an allele comprising polymorphisms other than the probe's "designated" polymorphism. Conversely, a probe-target hybridization may be unexpectedly enhanced when a probe, while displaying a significant mismatch with the target within its designated subsequence, matches a specific allele in a non-designated subsequence.

As with binarization generally, subpopulations are delineated by selection of a threshold. Particularly when assay signal distributions are not bimodal, threshold selection represents a critical initial step in the analysis.

In the context of HLA molecular typing, the requisite extensive analysis of interaction patterns and assignment of alleles currently relies to a substantial degree on the experience of specialists. These specialists and experts engage, usually with minimal computational support, in a time-consuming, difficult and often subjective process of interactively establishing, reviewing and editing ("redacting") allele assignments, often with reference to printed compilations of known alleles (e.g., the database maintained by the National Marrow Donor Program) and corresponding "hit tables."

As with molecular typing of leukocyte antigens and erythrocyte antigens, the reliable and rapid analysis and interpretation of complex probe-target interaction patterns represents a prerequisite for the meaningful validation of sets of genetic markers to validate these "predictors" of disease predisposition or treatment responsiveness in patient populations of sufficient size to permit statistically significant conclusions. Similar challenges arise in other areas, for example: in connection with the analysis of genetic polymorphisms in mutation analysis for carrier screening and diagnosis and associated risk assessment; and in connection with the assessment of predisposition to acquire genetic diseases of complex inheritance which may manifest itself in the form of an entire set of polymorphic markers or gene expression profiles.

A convenient software system invoking computational algorithms and robust procedures for automated pattern analysis and interpretation, and providing an integrated environment for the interactive review and redaction of assignments as well as data management and visualization would be desirable.

SUMMARY

Disclosed are methods and algorithms (and their implementation) supporting the automated analysis and interactive review and refinement ("redaction") of the analysis within an integrated software environment, for automated allele assignments. The implementation, preferably with a software system and a program referred to as the Automated Allele Assignment ("AAA") program, provides a multiplicity of functionalities including: Data Management by way of an integrated interface to a portable database to permit visualizing, importing, exporting and creating customizable summary reports; System Configuration ("Set-up") including user authorization, training set analysis and probe masking; Pattern Analysis including string matching and probe flipping; and Interactive Redaction combining real-time database computations and "cut-and-paste" editing, generating "warning" statements and supporting annotation.

Thresholding—Methods of selecting and refining thresholds are disclosed, including a generalization of the binary representation obtained by segregating probe intensity distributions into three or more subpopulations.

Initial Threshold Determination—A method of setting thresholds by way of analyzing a reference ("training") set and selecting is also disclosed, for each probe in a selected probe set, a threshold which maximizes the degree of concordance of assay results and assigned alleles with those provided for the training set. The method of determining the initial threshold settings also provides a figure of merit ("goodness") as the basis method of assessing the robustness of that threshold. A related method of initial threshold determination disclosed herein applies a binarization algorithm to individual probe intensity profiles.

Threshold Refinement: Pattern Matching—A method of refining thresholds by matching an experimental binary string ("reaction pattern") is disclosed, produced by application of initial threshold settings, with a compendium of reaction patterns corresponding to valid allele combinations. The software system herein supports a mode of altering ("flipping") specific bits within the experimental string ("word"). The program identifies probes, and probe combinations, as candidates for "flipping" in order to produce complete or partial concordance between the modified experimental "word" and the closest word, or words, in the dictionary. Flipping of a probe—for certain samples in the set under consideration—corresponds to a refinement in the threshold setting for that probe.

Probe Masking—Also disclosed is a program feature supporting a configuration ("set-up") mode in which selected probes can be temporarily excluded from analysis ("masked"). Assay signals produced by probes which do not contribute significantly to discriminating among alleles—or may be judged to produce intensity patterns of low reliability—can also be masked when analyzing the results, and then viewed only if their contribution is deemed necessary.

Allele Frequency Statistics—In another aspect, the software system provides a method for tracking and displaying the relative frequency of occurrence of allele groups (and combinations thereof).

Interactive "Redaction"—The software system provides an integrated environment to facilitate simultaneous access to the data being analyzed and databases and hit tables being consulted, for example in the course of redaction. "Cut-and-Paste" operations are provided in multiple screens to permit the rapid and convenient editing of automated ("program") assignments including an annotation function.

Confirmatory Testing for Resolution of Ambiguity—The program also accommodates additional information aiding in the resolution of ambiguities by way of group-specific amplification or by way of using elongation mediated analysis of polymorphisms (see "Multiplexed Analysis of Polymorphic Loci by Concurrent Interrogation and Enzyme-Mediated Detection" filed Oct. 15, 2002; Ser. No. 10/271,602).

Distributed Analysis: Processing, Analyzing, Interpreting, Archiving—The architecture of the software system supports a mode of distributed analysis, permitting different functions such as assay image recording, automated analysis, interactive redaction, and assessment and final "sign-off" and report generation to be performed by different individuals in different geographic locations. This mode of distributed analysis expands the capabilities of individual testing laboratories to expand their respective test menus without the requirement for local expertise pertaining to the many disparate areas of expertise. For example, testing center locations may be chosen so as to facilitate collection of patient samples, while board-certified physicians may review and release final test results from a different location, while serving multiple testing centers.

Also disclosed is a method and pseudocode for fully automated allele analysis, which is set forth below.

BRIEF DESCRIPTION OF THE DRAWINGS

FIG. 1B shows a threshold determination for one probe in a training set of probes, where the threshold value is plotted on the X axis, and the threshold measurement is on Y axis. The optimal threshold yields the maximum measurement in Y, which is 1 in this case.

FIG. 1C shows the system settings for a number of different HLA probes. The allele assignment tolerance (see FIG. 2) is entered in the text boxes. HLA-A is allowed a maximum 6 flips; HLA-B 8 flips; and HLA-DR 5 flips. Each probe can be assigned as required, high confidence, low confidence or not used. The core set of probes (see FIG. 3) consists of only the high confidence probes, while the expanded set of probes includes the high and low confidence probes. By changing the settings, one can interactively change the core set and expanded set. For instance, HA120 can be set as high confidence and HA121 as low confidence.

FIGS. 2A to 2C show, respectively, the normalized intensity ("ratio") for the probes HB103, HB123A, HB154, sorted in the order of increasing ratio to illustrate a discontinuity in the probe ratio profile. HB103 (FIG. 6A) has the largest difference in ratio profile. HB123A (FIG. 6B) has no obvious jump in profile. HB154 (FIG. 6C) has two jumps in the profile. In the reaction pattern, 8 indicates positive, 1 indicates negative (no signal) and 0 indicates the probe is not used.

FIG. 3 is an example of allele assignment, where the reaction pattern is shown in the first row, ranging from 0 to 8, and the hybridization string is the pattern shown in the columns. The columns 119, 121, 122, 135A, 142A and 145 are low confidence probes. Since there is only one suggested assignment, the expanded probe set is empty.

FIG. 4 is the reaction pattern and hit table for an exemplary reaction between probes and a target, showing also the screen shot of the program for performing manual redaction, allele assignment, and a place for inserting comments.

FIG. 7 is a screen shot illustrating the assignment summary information for a panel designated "03250443," and includes the panel name, sample name, sample position, allele assignment, flip probes, warning message and comments.

FIG. 8A is a probe ratio profile.

FIG. 8B is the numerical derivative showing the inflection points derived from FIG. 8A.

DETAILED DESCRIPTION

Figure 1A:
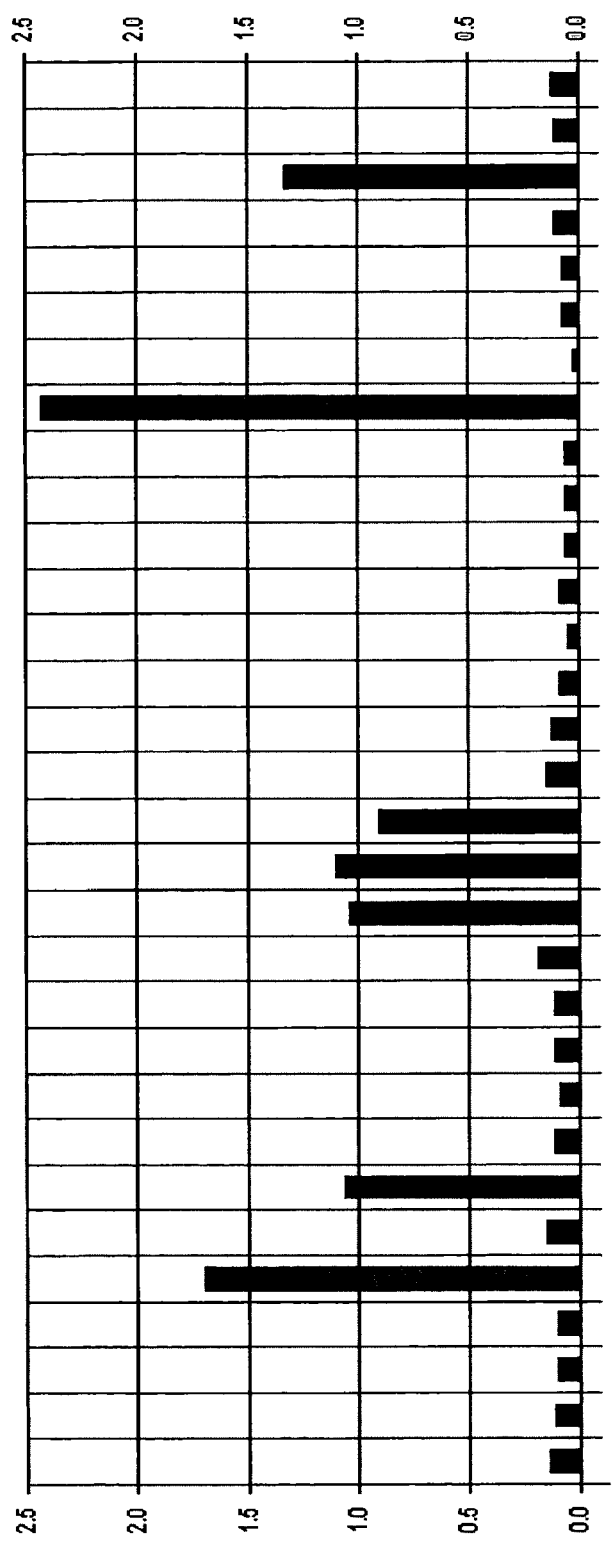
FIG. 1A illustrates a set of assay signal intensities recorded for probe HA109 in the analysis of a training set of samples. By an independent method, the normalized probe intensity was scored negative for samples marked "−" and positive for samples market "+".
Figure 5:
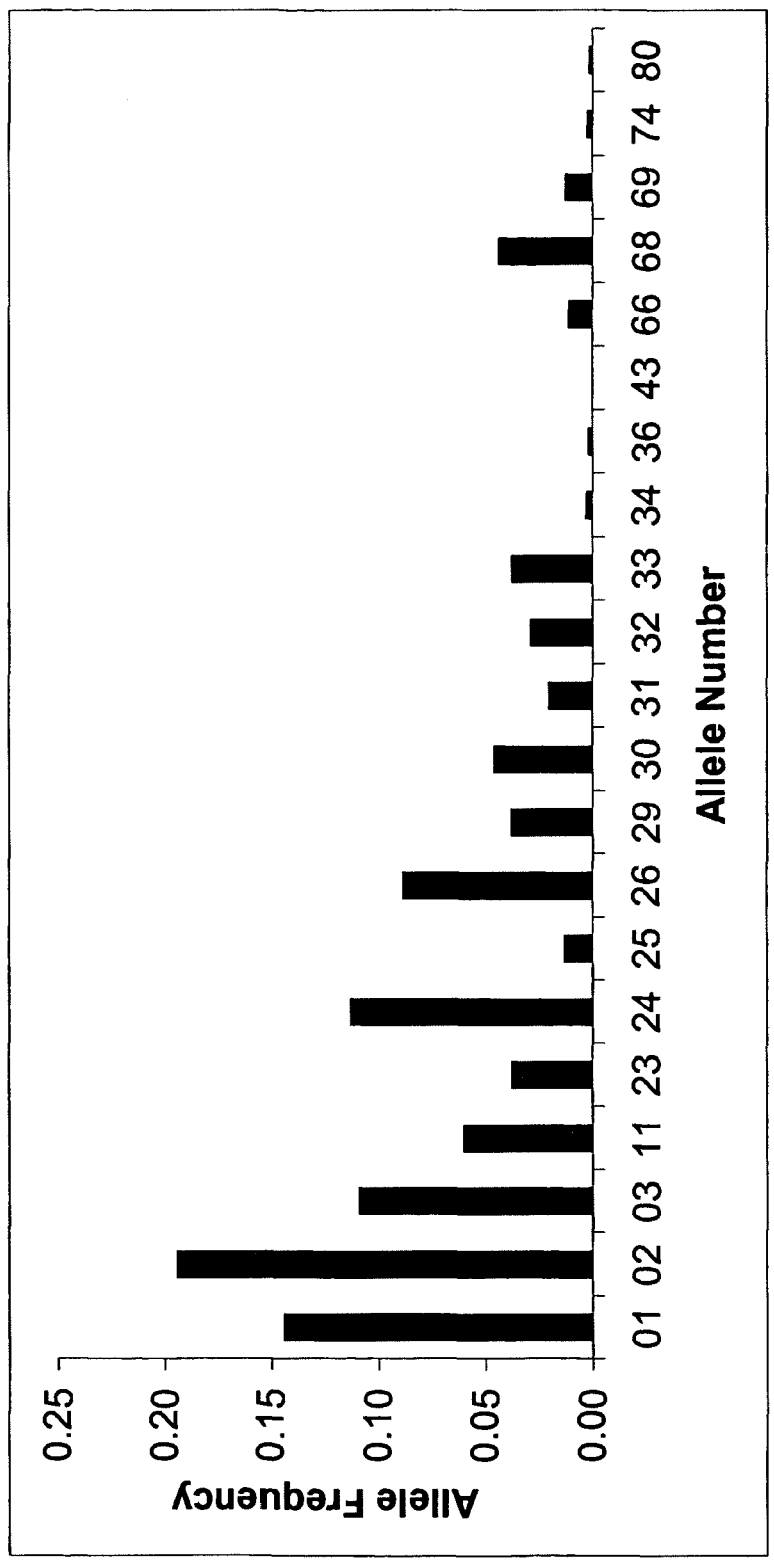
FIG. 5 is a bar-graph for the allele frequency distribution of a particular population.
Figure 6:
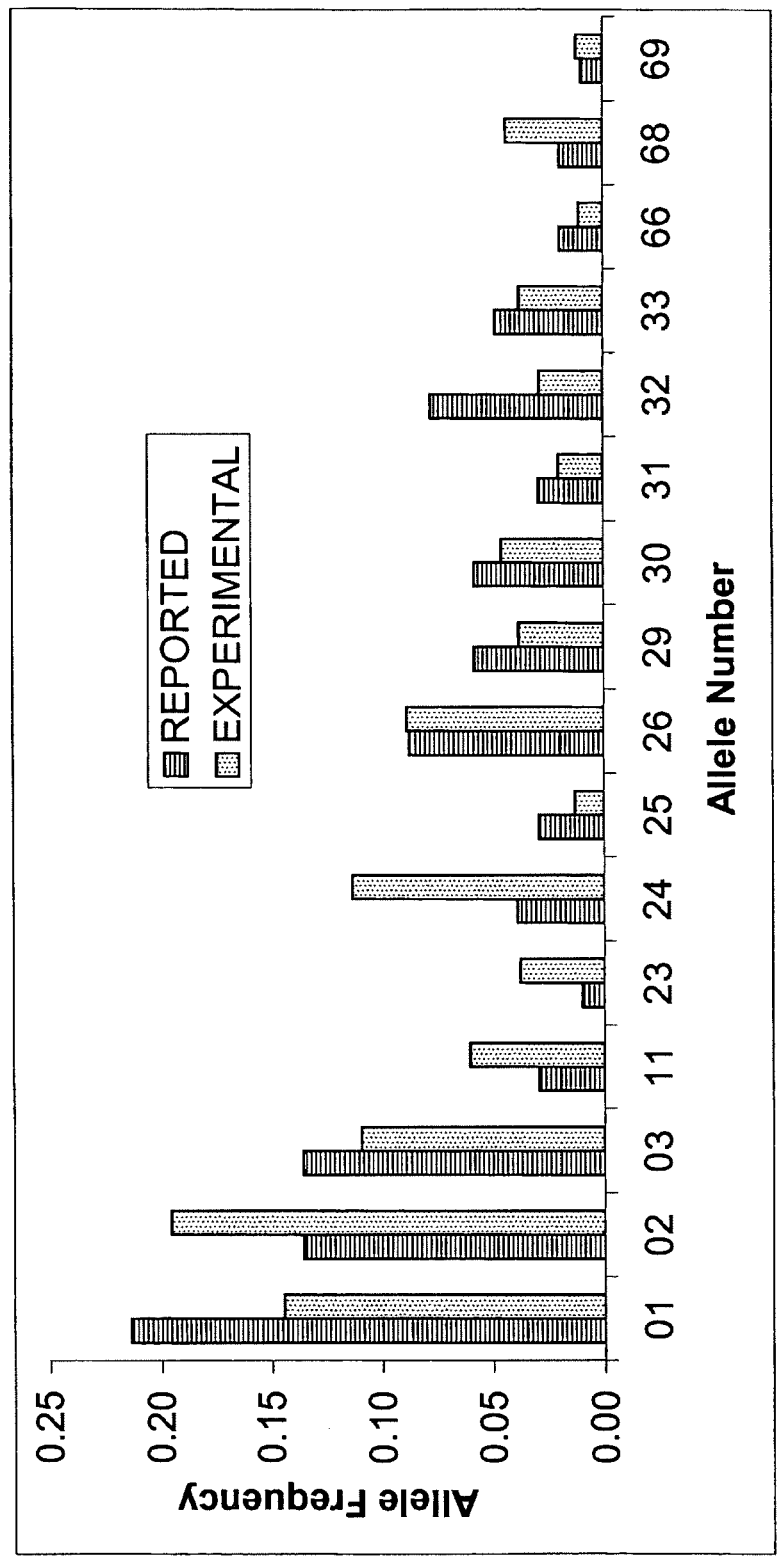
FIG. 6 is a bar-graph showing the comparison between reported genotyping studies of a allele distribution in a "Jewish Normal" population, and the experimental results for such population.

Following the recording of an assay signal intensity pattern for a given sample, a sequence of analytical steps is performed to identify the corresponding allele combination.

2.1 Conversion of Assay Intensity Patterns into Binary Strings

Normalized Assay Signal Intensities: Probe Intensity Profiles—Certain methods of probing polymorphisms within a target nucleic acid such as Elongation-mediated Analysis of Polymorphisms (eMAP™, also referred to herein as "capture-mediated elongation"), disclosed in co-pending U.S. patent application Ser. No. 10/271,602 (PCT/US02/33012) produce assay signals which rely on a molecular recognition process whose high specificity produces an approximately "binary" distribution of assay signals. In contrast, methods such as Hybridization-mediated Multiplexed Analysis of Polymorphisms (hMAP™, U.S. patent application Ser. No. 10/847,046) produce assay signal intensities reflecting the effective affinity governing the interaction of each probe in a set of multiple such probes with the target. To correct for variations in background, original target concentration or other experimental conditions, experimental signal intensities recording probe-target interactions are normalized using signals recorded from positive and negative control probes (and probe-target pairs) included in the reaction.

From each signal intensity, usually the mean value, $I_k$, for the k-th type of probe, including the positive control signal, $I_{PC}$, and the negative control signal, $I_{NC}$, is subtracted, and the result is divided by the corrected positive control signal to obtain a normalized intensity (ratio):

$$r=(I-I_{NC})/(I_{PC}-I_{NC})$$

To facilitate an assessment of the performance of any given probe in the panel, a probe intensity profile, also referred to herein as a ratio profile, is constructed by sorting the r-values recorded for that probe over a set of samples, typically 100 samples, for example, in ascending order. Examples of such profiles are shown in FIGS. 2A-2C, where FIG. 2A illustrates a profile displaying an abrupt transition of large amplitude from lower to higher r-values, whereas FIG. 2B illustrates a profile displaying a gradual transition of small amplitude.

For methods such as hMAP, the normalized signal intensities are first converted to a binary representation: if r exceeds a pre-set threshold, T, the corresponding binary score is positive, s=1 (also denoted herein as "8"), otherwise negative, s=−1 (also denoted herein as "1"). Methods of implementing this critical signal processing step are disclosed in the following subsections.

2.2 Determination of Thresholds: Binarization—An algorithm is disclosed for the determination and iterative refinement of binarization threshold settings. As is true for the analogous step in image analysis of converting gray-scale pixel intensities to "black-and-white" representation, binarization assigns normalized assay signal intensities to one of two subsets. This is unproblematic as long as the distribution of normalized signal intensities for a set of samples under consideration has a bimodal shape featuring well separated peaks: a threshold can then be placed almost anywhere between the two peaks without affecting the result; FIG. 2A corresponds to a bimodal histogram. However, in other cases, when separate peaks are not clearly resolved, binarization presents a source of uncertainty or potential error: the assignment of specific intensity values to one or the other subset will depend in a sensitive manner on the precise placement of the threshold; FIG. 2B corresponds to such a case.

Initial Threshold Settings: Analysis of "Training" Sets—Initial threshold settings can be based on the analysis of a reference or "training set". Preferably, reference samples are chosen to reflect characteristics of the group of samples of interest; for example the prevailing frequency of occurrence of allele combinations and haplotypes. Such information can provide additional constraints on likely allele assignments. Methods of automated collection and statistical analysis of sample population statistics are elaborated below.

A reference ("training") set of S samples, with independently determined and validated reference reaction pattern $\{\sigma_k, 1 \le k \le P_T\}$, and independently determined and validated allele assignments, is analyzed with a selected set of P probes, to obtain the normalized intensity (ratio) pattern $\{r_k; 1 \le k \le P\}$, and, for each probe, k, in the selected set (see also below), a threshold, $T_k$, is determined so as to maximize the concordance between the actual reaction pattern, $s_k=s_k(T)$, and the reference pattern $\{\sigma_k, 1 \le k \le P_T\}$.

That is, for each probe in the actual set, a threshold is determined for each probe by analysis of the normalized intensity profile over the training set of S samples so as to maximize the cross-correlation $C=\Sigma_i((r_i-T_k)\cdot\sigma_i)/\Sigma_i|(r_i-T_k)|$, $1 \le i \le S$. For each probe in turn, to find the maximum of the function C, the threshold setting, $T_k$, is increased stepwise until the sign of the quantity $r_i-T_k$ matches that of the corresponding bit, $\sigma_i$, in the reference pattern. For probes used in the assay, but not in the interrogation of the training set, a reaction pattern is "back-calculated" from the hit table using the assigned alleles. FIG. 1B illustrates the shape of the function $C=C(T)$, $r_{min} \leq T \leq r_{max}$. The threshold setting is chosen so as to maximize the function C.

The pseudocode for determining the initial threshold setting is as follows:

```
/*
** ρ is the normalized intensity ("ratio") pattern for a given sample;
binarization will
** convert each intensity pattern into a reaction pattern composed of P
bits; there will
** be S such patterns;
** π is the set of probe profiles; there will be P such profiles, each with a
threshold,
T;
** τ is the set of optimal (initial) thresholds, to be determined by
maximization of C;
*/
GenerateProbeProfiles(ρ, S, π, P)    /* sort reaction patterns by
                                        probe
*/
{
    FOR( each probe )
    {
        ExtractIntensity( from reaction patterns )
        SortProbeIntensities( );
    }
}
/*
** maximize C = Σ_i ((r_i – T_k) * σ_i) / Σ_i /(r_i – T_k)/
** the r_i denote the elements of the ratio profile R */
*/
FindThreshold(R, Σ, S)
{
    C_max = 0;
    T = r_min;
    DO
    {
        IF( (C = Σ_i ((r_i – T) * σ_i)/ Σ_i /(r_i – T) /) > C_max) C_max = C;
        T = T + ΔT;
    }WHILE( T <= r_max);
    Return( T );
}
DetermineInitialThresholds( )
{
    GenerateProbeProfiles(ρ, S, π, P)
    FOR( each of P ratio profile, π_k)
    {
        τ_k = FindThreshold( π_k, Σ_k, S)
    }
    Return(τ);
}
```

"Goodness" of Threshold Settings—Threshold settings may be robust for some, but less robust for other probes in the set. That is, when the composition of the two sample subpopulations, generated by application of a threshold T to the probe intensity profile changes in response to a small change in the value T to T+ΔT or T–ΔT, where ΔT/T<<1, then that threshold is not robust, and the statistical confidence is low.

To permit the placement of confidence intervals on individual threshold settings, a figure of merit ("goodness of threshold") also is disclosed herein. This is derived from the shape of the peak of the function $C=C(T)$, produced in the course of maximizing the cross-correlation with a set of assignments for a training set. The steeper the peak in the function, the more sensitive the selected value of T to small variations in T, as illustrated in FIG. 1B.

A "goodness", G, of a threshold selected by the method of maximizing the cross-correlation, C, as just described, is defined as follows:

$$G=(C_L+C_R)/2C_{Max},$$

wherein $C_{Max}$, $C_L$ and $C_R$ respectively denote the maximum value of C, $C_L$ the value of C obtained when decreasing the threshold value by 30%, and $C_R$ the value of C obtained when increasing the threshold value by 30%.

Weights—Once a threshold, T, has been determined, the probe intensity profile, $\{r_i, 1 \leq i \leq S\}$ can be recast into a scaled form, $w_i=(r_i-T)/T$, wherein the weights, $w_i$, represent the relative magnitude of individual (normalized) signal intensities. The software system described herein (designated "AAA") tracks weights and displays them in one of several formats, for example, by a simple classification into "Close" ("C", $w \leq 0.5$) or "Distant" ("D") in connection with bit "flipping", as further discussed below.

2.3 String Matching: Correlations within Probe-Target Interaction Patterns

The analysis of experimental intensity patterns aims to identify, or approximately identify, the underlying target allele(s). To that end, intensity patterns are binarized by application of a set of thresholds, and the resulting binary string ("reaction pattern") is compared to combinations of pairs of such strings corresponding to known alleles listed in a "hit table." Each entry in a "hit table" represents a valid allele and provides a binary sequence in which each position contains a score of "Matched" or "Mismatched" referring to the degree of complementarity of the allele with the probe in that position (see FIG. 3A). Alleles are designated by 4-digit codes and are grouped by the leading 2-digits into antigen groups.

Error Correction by String Matching: "Flips"—To identify the target alleles, the binary reaction pattern, $\{s_k, 1 \leq k \leq P\}$ is compared, bit by bit, to all reference strings representing 2-allele combinations; these are generated by application of an OR operation to the hit table entries. The matching of entire bit strings enforces correlations and affords a method of "error correction" by way of inverting ("flipping") individual bits in the string as judged necessary in order to produce a match with a valid reference string. This process is akin to checking typographical errors so as to produce valid words: by changing the letter "t" in "valit" to "d", a valid English word is obtained; another valid English word is obtained by changing "i" into "u" and "t" into "u", but "valit" is "closer" to "valid" than it is to "value", and the former therefore more likely represents the desired word.

In analogous manner, the AAA program is designed to find the closest valid bit strings ("words") representing valid alleles, as identified, for example, in a database which can be entered in the AAA program. The AAA program lists the "closest" valid strings, grouped by common 2-digit "group" codes, in the order of increasing Hamming distance (i.e., the number of mismatched bits) from the experimental string. Specifically, the program identifies the mismatched bits and suggests the requisite "flips", namely "1 to 8" or "8 to 1," which would produce a complete match between the experimental string and those additional valid strings within a preset maximal Hamming distance.

The AAA program also permits a deeper search of the space of reference strings in order to produce a list of "near-matches" (see drop-down menu illustrated in FIG. 4). This extended analysis frequently reveals possible alternate strings representing more likely allele assignments based on such additional considerations as the frequency of occurrence of certain alleles or haplotypes in the population of interest. This feature substantially reduces the time and effort expended on interactive editing.

Distance between Strings—Within each group, strings corresponding to valid allele combinations are ranked in the order of an increasing weighted Hamming distance from the reaction pattern. This distance function is defined in terms of the weights, $w_i=r_i-T)/T$, associated with the mismatched probes. For example, assuming there to be M mismatched probes, a possible distance function is:

$$X^2=(1/M)\Sigma_{mismatched\ probes}w^2$$

2.4 Iterative Threshold Refinement

Ideally, the string matching procedure just described will produce an unambiguous match between the reaction pattern and a string representing a valid allele combination. However, even when a perfect match is called, this call may not be unambiguous if it involves low weights for one or more of the probes. That is, in practice, the reaction pattern may contain false negatives or false positives, depending on the threshold setting for individual probes and the weights of normalized intensities. Especially the statistical confidence associated with threshold settings of probes having continuous ratio profiles for the set of samples under consideration will be low, and it is therefore beneficial to have a process of adjusting ("fine tuning") such threshold settings.

The string matching procedure provides a basis for the refinement of initial thresholds. After all, flipping a probe is equivalent to adjusting the corresponding threshold so as to change the sign of the normalized ratio relative to the threshold setting. That is, if, following an initial pass of automated allele assignment for a set of samples, a certain probe is consistently "flagged" as either false positive or false negative, this is an indication that a threshold refinement for that probe is in order. Accordingly, threshold optimization involves an iterative process of adjusting the threshold settings of one or more "flagged" probes so as to minimize the total number of flips identified by the AAA program. Because this threshold optimization process is based on string matching, rather than on the inspection of individual probe ratio profiles, as in the step of setting initial thresholds, threshold optimization reflects the correlations between multiple probes in the set and improves statistical confidence. Threshold refinement can be performed on a continuing basis using analyzed samples as a continually expanding reference set. In this application, each new set of samples becomes a new training set.

In general, the number of flips even after threshold optimization will remain finite. In such cases, the weights associated with indicated flips must be taken into account. The AAA program conveniently designates ratios of "flips" as either "Close" (C, r≤0.5) to threshold, or "Distant" (D) from threshold. The cut-off represents a tunable performance parameter which may be set more or less conservatively, a more conservative setting generally implying a greater degree of interactive review and editing, as discussed in greater detail below. A requirement for flipping "distant" probes, i.e. those having a large weight, in order to obtain a match represents an indication that a new allele may be in hand.

The pseudocode below summarizes the threshold refinement procedure as implemented in the AAA software system of the invention.

```
/* calculate allele assignment for a list of samples, then
/* identify and analyze the flipped probes for that list
    CalculateAssignment(SampleLists);
    GetFlips(SampleLists);
    AnalyzeFlips( );
/* Select probes requiring threshold refinement
    ProbeSet = SelectProbes( );
/* for each probe, find the optimal threshold, by minimizing the number of total flips
    FOR each(probe in ProbeSet)
    {
        T_0 = GetInitialThreshold(probe);              /* get initial threshold
        FOR( T = T_0-range; T<= T_0+range; T+=deltaT)  /* adjust threshold
        {
            RecalculateAssignment(SampleLists);
            TotalFlips = AnalyzeFlips( );              /* re-analyze flipped
                                                          probes and get the
                                                          number of total
                                                          flips
        }
        FindMinTotalFlips( );                          /* find min total flips
        /* the new threshold will be the one minimizing total flips
        T_new = GetNewThreshold(probe);
    }
```

Additional features included in the AAA software system are set forth below.

Modification of Probe Sets—A particular binary reaction pattern may match with more than one allele, and often will if the bit string has only a few elements ("8s" and "1s") and the target includes multiple polymorphic regions. The degree of ambiguity is calculated by simply enumerating the number of unresolved ("degenerate") alleles. Lengthening of the string, by inclusion of additional probes, can provide a means to attain increased resolution in order to resolve ambiguities.

Probe Masking: Core and Expanded Probe Sets—Described below is a method for interactive designation of core sets and expanded sets of probes, along with a "probe masking" feature, which can be used to correct for signals from those probes which do not perform as well as others. In probe masking, results from those probes which hybridize to a wide variety of samples, rather than only to particular samples with particular alleles, are ignored. Such a wide level of hybridization may result from cross-hybridization or from probes targeting widely expressed subsequences.

The AAA software system provides a configuration ("setup") screen permitting the user to designate probes within a panel to be part of a core set or an expanded set. The probe-masking function prompts users to enter a list of probes which are to be ignored ("masked") in the first pass of automated allele assignment—that is, the program calculates assignments first on the basis of a core set of probes which hybridize more narrowly. The objective of using the core set is to obtain a group-level assignment for alleles (i.e., a group of several possible alleles) using probes which provide group level discrimination with a high confidence level.

In the probe masking mode, the AAA program first performs group-level assignments using only the core set of probes. In an (optional) second pass, the assignment can be refined by repeating the calculation with the extended set which contains all the probes in the core set, as well as the remaining less-reliable probes. The second pass will produce additional assignments that remain compatible with the assignments made in the first pass. The program also performs this second pass whenever the first pass does not produce a unique group level assignment.

The extended set is useful in guiding "redaction" and allows the user to select the most likely allele assignment. In some cases, the complementary (e.g., antisense) version of one or more probes (and the corresponding transcripts or amplicons) may need to be generated and used, to avoid excessive cross-hybridization. In such cases, the non-complementary probes are then excluded from the first and/or second pass.

Population Statistics: Analysis of Allele Frequency Distribution—The rate of recurrence of each allele is dependent on the population over which HLA typing is being conducted. For a panel containing a large number of samples, the occurrence of a particular allele is representative of its abundance or rarity in the entire population of interest. The distribution of alleles in a population of known ethnicity can be calculated for a panel.

The results for a set of panels from the AAA database program were used to calculate allele frequency. The program assigns each sample a set of two alleles based on its reaction pattern over the whole probe set. The frequency calculations are based on two digit allele assignments. The first two digits of the allele assignments for all samples are extracted and compiled into a single vector. A histogram is calculated which lists each allele with the number of times it is encountered in the panel (its count). The frequency is calculated as the count is normalized by the total number of assignments.

One purpose of tracking allele frequency statistics, as implemented in the program, is to provide editing aids, such as warning flags whenever a rare allele is identified. This will help in case of degenerate assignments, where more than one unique assignment is possible. In such cases, those assignments which involve rare alleles can be eliminated manually. In case of single assignments, such flagging of rare alleles ensures that the assignments are manually checked, and either verified, or flipped.

Interactive "Redaction"—Following automated allele assignments using the program and the methods described above, the putative assignments may be "edited" against either an allele database indicating known alleles, or by a combination of experimental data for alleles (which forms a continually expanding reference set) and an allele database. An illustration of key steps is given in an Example.

Weights represent a measure of confidence in the bit assigned any given probe intensity: bits are less likely to be incorrectly assigned, and flips therefore are less likely to be executed, the larger the weight of a specific probe intensity signal (or a suitable function based on those weights). Thus, weights can help guide interactive redaction.

Another guide is available in the form of allele frequencies in the entire population, or in a sub-population being monitored. Again, the analyzed samples form a continually expanding reference database, which are added to the training set whose allele (and haplotype) frequencies are updated in real-time.

Detection of New Alleles—New alleles may be indicated by targets which produce binary reaction patterns which can be matched to existing reference strings representing combinations of known alleles only by flipping probes having significant weights. This is discussed in greater detail in Example I (Allele Assignment) below.

Generalization of Binary Representation—The AAA program also accommodates representations of intensity patterns other than the binary representation and the corresponding binary strings ("words").

Three-Letter Alphabet and Hit Tables—As an immediate generalization, consider representations invoking an alphabet of three or more letters. Such a three-letter representation naturally arises when a pair of degenerate probes is provided for one or more of the designated polymorphic target sites. For example, in a novel approach invoking the format of Elongation-mediated Multiplexed Analysis of Polymorphisms (eMAP) to analyze mutations in a set of genes encoding human blood group antigens, a pair of degenerate elongation probes is provided for each of the designated variable sites. The members of the pair differ at or near their 3'termini, one member designed to match the expected normal target allele, the other member designed to match the expected variant allele. Only the elongation probe matching the target is elongated in a manner producing a corresponding assay signal associated with the elongation products (see U.S. application Ser. No. 10/271,602). That is, eMAP produces one of three possible values at each designated polymorphic site, namely normal, variant ("homozygous" mutant), or heterozygous.

The representation reflects the three possible outcomes of the eMAP determination at each designated site, namely:

normal probe matched, variant probe mismatched: normal—denoted by 1 normal probe mismatched, variant probe matched: variant—denoted by $-1$ normal probe matched, variant probe matched: heterozygous—denoted by 0

This reflects the possible combinations of the underlying alleles, namely AA (normal or "wildtype"), BB (variant, homozygous) and AB or BA (heterozygous). A hit table for the sites of interest will be composed of letter codes which are combined by the rules just stated.

Example III illustrates the use of a 3-letter alphabet (1, 0, $-1$) to represent observed biallelic combinations.

Upper and Lower Thresholds—A three letter representation also arises, in analogous manner, in connection with the introduction of an upper and a lower threshold. For each probe under consideration, an assay signal intensity below the lower threshold corresponds to a mismatch with both target alleles, an assay signal intensity above the lower, but below the upper threshold corresponds to a match with one, but not the other allele, and an assay signal intensity above the upper threshold corresponds to a match with both alleles.

The designation of negative and positive bits can be made with increased confidence if two thresholds, which segregate normalized assay intensities recorded for any given probe into three sub-populations, are defined. The three sub-populations would be those for which: (i) a given probe is mismatched to both assigned alleles (1,1), (ii) a probe is matched to one allele (1, 8; 8, 1), and (iii) a probe is matched to both alleles (8, 8).

Because of the possible existence of the second (8, 8) threshold, it would be possible to establish a threshold for a particular probe incorrectly, that is, the threshold for a (8, 8) probe as distinguished from a (8, 1) probe, could be incorrectly identified as the threshold for a (8, 1) probe distinguished from a (1, 1) probe. Such incorrect threshold designations can be spotted and corrected by continued refining and expansion of the training set, and/or by double-checking the allele assignments against the known allele database references and ensuring consistency.

Another situation in which needs to be considered, is that normalized assay intensities recorded for any given probe which are above the second (highest) threshold, could be due to reaction with the designated target subsequence on both alleles (indicating a homozygote), or could be due to reaction with two independent alleles, which coincidentally, are reactive with that probe. Again, this situation can be spotted and corrected by continued refining and expansion of the training set, and/or by double-checking the allele assignments against the known allele database references.

In determining the location of thresholds, where there is more than one threshold for a particular probe, one can examine the ratio intensity profiles (as shown in FIGS. 2A to 2C; see also FIGS. 8A and 8B). But if there is no sharp inflection in the profile, as illustrated clearly in FIG. 2B, one can locate the inflection points, and thus the thresholds, by taking the numerical derivative using a convolution filter. The results of taking the numerical derivative in this manner is shown in FIG. 8A, which is a ratio profile, and FIG. 8B, which is the numerical derivative showing the inflection points derived from FIG. 8A.

Digitization of Analog Patterns—Normalized intensities, instead of being binarized, also can be digitized with any desirable degree of higher precision than that afforded by binarization. For example, instead of two subpopulation, one might chose to segregate intensities into eight subpopulations or 16 subpopulations. Inherent in this representation is the information represented in the form of weights in the binary representation discussed herein above. Each digitized normalized intensity in fact represents a measure of the coaffinity of a particular probe-target interaction (see U.S. application Ser. No. 10/204,799 "Multianalyte Molecular Analysis"; WO 01/98765). Experimental digitized reaction patterns, and reference digitized patterns are compared by means of computing cross-correlations using standard methods.

Multi-user Remote Access, Application Serving—Use of a program also allows the establishing of a network to permit remote analysis, redaction and reporting of results of allele assignment. For example, a database which forms part of the AAA software environment, may be accessed via a secure network connection. The AAA program also supports an application service mode permitting interactive editing from a location other than the location of the experimental laboratory.

Preferred Embodiment of Multiplexed Analysis: Random Encoded Array Detection—In one format of multiplexed analysis, detection probes are displayed on encoded microparticles ("beads"). Labels are associated with the targets. The encoded beads bound to the probes in the array are preferably fluorescent, and can be distinguished using filters which permit discrimination among different hues. Preferably, sets of encoded beads are arranged in the form of a random planar array on a planar substrate, thereby permitting examination and analysis by microscopy. Intensity of target labels are monitored to indicate the quantity of target bound per bead. This assay format is explained in further detail in International Publication No. WO 01/98765 entitled: "Multianalyte molecular analysis," incorporated by reference. Several methods of producing optical signatures are available, for example by capture of labeled targets or by target-mediated probe elongation (eMAP), the latter preferably performed by using immobilized allele-specific oligonucleotides capable of priming a polymerase-catalyzed elongation reaction. (see, e.g., International Publication No. WO 03/034029). One or more suitable targets are produced, for example, by reverse transcription of RNA and/or amplification of genomic DNA, optionally followed by additional steps such as fragmentation (see U.S. Provisional Application 60/515,413), denaturation or strand selection (U.S. application Ser. No. 10/847,046).

Subsequent to recording of a decoding image of the array of beads, the array is exposed to the targets under conditions permitting capture to particle-displayed probes. After a suitable reaction time, the array of encoded particles is washed to remove remaining free and weakly annealed targets. An assay image of the array is then taken to record the optical signal of the probe-target complexes of the array (or to record the signal from elongated probes, in the event capture-mediated elongation is the assay format being used). Because each type of particle is uniquely associated with a sequence-specific probe, the decoding step permits the identification of annealed target molecules determined from fluorescence of each particular type of particle.

A fluorescence microscope is used for decoding. The fluorescence filter sets in the decoder are designed to distinguish fluorescence produced by encoding dyes used to stain particles, whereas other filter sets are designed to distinguish assay signals produced by the dyes associated with the targets. A CCD camera may be incorporated into the system for recording of decoding and assay images. The assay image is analyzed to determine the identity of each of the captured targets by correlating the spatial distribution of signals in the assay image with the spatial distribution of the corresponding encoded particles in the array.

In this format of multiplexed analysis, there is a limitation on the number of probe types, in that the total number of bead types in the array is limited by the encoding method used (e.g., the number of distinguishable colors available) and by the limits of the instrumentation used for interpretation, e.g., the size of the field in the microscope used to read the array. One must also consider, in selecting probes, that certain probes hybridize more efficiently to their target than others, under the same conditions. Hybridization efficiency can be affected by a number of factors including interference among neighboring probes, probe length and probe sequence, and, significantly, the temperature at which annealing is conducted. A low hybridization efficiency may result in a false negative signal. Accordingly, an assay design should attempt to correct for such low efficiency probe/target annealing.

After an actual assay has been performed, the Array Imaging System (as described in U.S. application Ser. No. 10/714,203, incorporated by reference) can be used to generate an assay image, which can be used to determine the intensity of hybridization signals from various beads (probes). The assay image can then be applied by a system for automatic allele assignment, as described herein.

EXAMPLES

I. Allele Assignment—By way of illustration (see also the "screen shot illustration" in FIG. 3), AAA, using the core probe set of probes, lists two suggested group allele assignments, namely A*03+A*29 and A*29+A*74. The two groups are ranked in the order of the weights of flipped probes. The lower the weight, the higher the rank of the groups. If the core probe set produces degenerate suggested assignments, as in this case, the analysis is automatically repeated using the expanded probe set. This second pass produces a suggested assignment of A*03+A*29 which would require the flipping of HA120+, indicating that HA120 may represent a false positive. The reaction pattern and hit table (for HLA-A alleles) also are displayed in the screen shot. In the reaction pattern, 8 indicates the probe is positive, 1 negative and 0 means the probe is not used.

In the manual redaction mode, the user can edit the initial allele assignments by checking the known references for the alleles identified in the core and expanded sets, and then conforming the bit strings to those expected from the known alleles. Verifying the experimental results against the known alleles in this manner provides a validation of the assay results, and a means to edit the bit string. User picks A*03011 and A*2901101 as assignment, HA120 as flip probe in manual redaction mode in FIG. 4.

Example II

Allele Frequency Statistics 1155 samples were screened using in an HLA-A panel, and the sample intensity patterns were analyzed using the AAA program to obtain two-digit allele group assignments. The count and relative frequency of occurrence of group calls calculated by the AAA program are shown in Table 1, immediately below.

The bar-graph for the following distribution is shown in FIG. 1. It is evident the alleles 01, 02 and 03 are much more abundant in this population whereas alleles 36, 43 and 80 are comparatively rare.

Example III

Assignment Summary Information Screen Shot

The screen shot in FIG. 3 illustrates the assignment summary information for panel 03250443. It includes panel name, sample name, sample position, allele assignment, flip probes, warning message and comments. The allele assignment lists the allele level assignment by computer algorithm. The flips and warning messages will be displayed according to computer assignment as well. If there is manual redaction, the allele assignment will be by the manual redactor's choice pick. See FIG. 4 for an illustration of manual redaction. The comment and flips input during any manual redaction are also displayed. The flip probes will be inserted to a (manual) string in the end, which indicates it is generated by manual redaction.

The software lists the first two digit of the allele assignment and the following digits, if applicable. For instance, A*24 (020101) indicates the two digit call is A*24. The summary information window displays all vital information in one window, which makes it easy to examine and navigate through different samples.

Example IV

Three-Letter Alphabet: Blood Group Antigen Molecular Typing

In a set of approximately 500 clinical samples and controls, several allele combinations were identified by an eMAP assay design, designed to probe minor blood group antigens including Duffy (FYA/FYB), GATA, Landsteiner-Weiner (LWA/LWB), Colton (CoA/CoB), Scianna (SC1/SC2), Diego (DIA/DIB) and Dombrock (DoA/DoB), the latter comprising three mutations. See Table 2 below.

| Allele # | Count | Frequency |
| --- | --- | --- |
| 01 | 332 | 0.144 |
| 02 | 448 | 0.194 |
| 03 | 251 | 0.109 |
| 11 | 139 | 0.060 |
| 23 | 86 | 0.037 |
| 24 | 260 | 0.113 |
| 25 | 30 | 0.013 |
| 26 | 203 | 0.088 |
| 29 | 87 | 0.038 |
| 30 | 105 | 0.045 |
| 31 | 46 | 0.020 |
| 32 | 66 | 0.029 |
| 33 | 86 | 0.037 |
| 34 | 6 | 0.003 |
| 36 | 4 | 0.002 |
| 43 | 0 | 0.000 |
| 66 | 25 | 0.011 |
| 68 | 100 | 0.043 |
| 69 | 28 | 0.012 |
| 74 | 5 | 0.002 |
| 80 | 3 | 0.001 |
|  | 2310 |  |

TABLE 2

| Observed Allele Combinations of Minor Human Blood Group Antigens | | | | | | | | | |
| --- | --- | --- | --- | --- | --- | --- | --- | --- | --- |
| Sample ID | FYA/FYB | GATA | LWA/LWB | COA/COB | SC1/SC2 | DIB/DIA | DO-793 | DO-624 | DO-378 |
| N21 BAS | −1 | −1 | 1 | 1 | 1 | 1 | −1 | −1 | −1 |
| N40 BAS | −1 | 0 | 1 | 1 | 1 | 1 | −1 | −1 | −1 |
| M17 | 0 | 0 | 1 | 1 | 1 | 1 | −1 | −1 | −1 |
| A10 | −1 | 1 | 1 | 1 | 1 | 1 | −1 | −1 | −1 |
| A4 | 0 | 1 | 1 | 1 | 1 | 1 | −1 | −1 | −1 |
| A1 | 1 | 1 | 1 | 1 | 1 | 1 | −1 | −1 | −1 |
| N39 BAS | −1 | −1 | 1 | 1 | 1 | 1 | −1 | −1 | 0 |
| N71 | −1 | 0 | 1 | 1 | 1 | 1 | −1 | −1 | 0 |
| N62-BAS | 0 | 0 | 1 | 1 | 1 | 1 | −1 | −1 | 0 |
| N66-BAS | −1 | −1 | 1 | 1 | 1 | 1 | −1 | −1 | 1 |
| 1 | −1 | 0 | 1 | 1 | 1 | 1 | −1 | −1 | 1 |
| N72 | −1 | 1 | 1 | 1 | 1 | 1 | −1 | −1 | 1 |
| M12 | −1 | 1 | 1 | 1 | 1 | 1 | −1 | −1 | 1 |
| 16 | −1 | −1 | 1 | 1 | 1 | 1 | 0 | 0 | −1 |
| 34 | −1 | 0 | 1 | 1 | 1 | 1 | 0 | 0 | −1 |
| A21 | −1 | 1 | 1 | 1 | 1 | 1 | 0 | 0 | −1 |
| N34 BAS | 0 | 0 | 1 | 1 | 1 | 1 | 0 | 0 | −1 |
| A28 | 0 | 1 | 1 | 1 | 1 | 1 | 0 | 0 | −1 |

TABLE 2-continued

Observed Allele Combinations of Minor Human Blood Group Antigens

| Sample ID | FYA/FYB | GATA | LWA/LWB | COA/COB | SC1/SC2 | DIB/DIA | DO-793 | DO-624 | DO-378 |
|---|---|---|---|---|---|---|---|---|---|
| A14 | 1 | 1 | 1 | 1 | 1 | 1 | 0 | 0 | −1 |
| N70 | −1 | −1 | 1 | 1 | 1 | 1 | 0 | 0 | 0 |
| A6 | 0 | 1 | 1 | 1 | 1 | 1 | 0 | 0 | 0 |
| A7 | 1 | 1 | 1 | 1 | 1 | 1 | 0 | 0 | 0 |
| N78-BAS | −1 | −1 | 1 | 1 | 1 | 1 | 0 | 0 | 1 |
| 2 | −1 | 1 | 1 | 1 | 1 | 1 | 1 | 1 | 0 |
| M23 | 0 | 1 | 1 | 1 | 1 | 1 | 1 | 1 | 0 |
| U79 | 1 | 1 | 1 | 1 | 1 | 1 | 1 | 1 | 0 |
| N35 BAS | −1 | −1 | 1 | 1 | 1 | 1 | 1 | 1 | 1 |
| N51 | −1 | 0 | 1 | 1 | 1 | 1 | 1 | 1 | 1 |
| A9 | −1 | 1 | 1 | 1 | 1 | 1 | 1 | 1 | 1 |
| 26 | −1 | 1 | 1 | 1 | 0 | 1 | 1 | 1 | 1 |
| 62 | −1 | 1 | 1 | 1 | 1 | 1 | 1 | 1 | 1 |
| N51-BAS | 0 | 0 | 1 | 1 | 1 | 1 | 1 | 1 | 1 |
| A25 | 0 | 1 | 1 | 1 | 1 | 1 | 1 | 1 | 1 |
| N7 BAS | 1 | 1 | 1 | 1 | 1 | 1 | 1 | 1 | 1 |

Example V

Establishing Relationships to Diseases and Conditions

Allele assignments determined by the foregoing methods can also be used to establish risk or presence of diseases or conditions. It is well known that certain immune disorders are associated with the HLA locus. The associated alleles can be typed, if known, and if unknown, the methods described herein can be used to establish an allele database to indicate risk or presence of diseases or conditions. The database can be continually updated based on monitoring of patients whose samples were used in the database; i.e., as some develop the disease, their alleles can be analyzed to determine commonality of those with a particular disease or condition.

It should be understood that the terms, expressions and examples herein are exemplary and not limiting, and that the invention is defined only in the claims which follow, and includes all equivalents of the subject matter of the claims. The method steps in the claims are not necessarily in order, and unless specified in the claim, may be carried out in any order, including that specified in the claims.

What is claimed is:

1. A method comprising:
   (i) providing a set of primers that generate targets from genomic regions which include a polymorphic locus of interest;
   (ii) providing an expanded probe set comprising a core subset of probes that hybridize only to particular targets with particular alleles and a second subset of probes that hybridize to multiple targets;
   (iii) exposing the targets to the expanded probe set under reaction conditions such that hybridization of targets and probes generates a signal;
   (iv) masking the signal of hybridization of targets and members of the second subset of probes; and
   (v) performing initial allele group assignments based only on the signal of hybridization of targets and members of the core subset of probes
   (vi) performing, after step (v), allele group assignments based on the signal of hybridization of targets and the second subset of probes.

2. The method of claim 1, further comprising making final allele assignments where allele group assignments made based on the second probe set agree with allele group assignments made based on the first subset of probes.

* * * * *